(12) United States Patent
Sakaguchi et al.

(10) Patent No.: US 9,613,289 B2
(45) Date of Patent: Apr. 4, 2017

(54) X-RAY DIAGNOSIS APPARATUS AND IMAGE PROCESSING APPARATUS

(71) Applicant: Toshiba Medical Systems Corporation, Otawara-shi (JP)

(72) Inventors: Takuya Sakaguchi, Utsunomiya (JP); Kunio Shiraishi, Otawara (JP); Kyojiro Nambu, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 160 days.

(21) Appl. No.: 14/547,470

(22) Filed: Nov. 19, 2014

(65) Prior Publication Data

US 2015/0154771 A1 Jun. 4, 2015

(30) Foreign Application Priority Data

Dec. 2, 2013 (JP) ................. 2013-249550

(51) Int. Cl.
*G06K 9/18* (2006.01)
*G06K 9/46* (2006.01)
*A61B 6/12* (2006.01)
*G06T 7/00* (2017.01)
(Continued)

(52) U.S. Cl.
CPC .............. *G06K 9/4604* (2013.01); *A61B 6/12* (2013.01); *A61B 6/485* (2013.01); *A61B 6/504* (2013.01); *A61B 6/52* (2013.01); *G06T 7/003* (2013.01); *A61B 6/463* (2013.01); *A61B 6/467* (2013.01); *A61B 6/469* (2013.01); *G06K 2009/3291* (2013.01); *G06K 2209/057* (2013.01); *G06T 2207/10016* (2013.01); *G06T 2207/10116* (2013.01); *G06T 2207/30101* (2013.01); *G06T 2207/30204* (2013.01)

(58) Field of Classification Search
None
See application file for complete search history.

(56) References Cited

U.S. PATENT DOCUMENTS

| 8,594,271 B2 | 11/2013 | Sakaguchi et al. |
| 2008/0221439 A1 | 9/2008 | Iddan et al. |
| 2008/0221440 A1 | 9/2008 | Iddan et al. |

(Continued)

FOREIGN PATENT DOCUMENTS

| JP | 2005-510288 | 4/2005 |
| JP | 2010-131371 | 6/2010 |

*Primary Examiner* — David H Chu
(74) *Attorney, Agent, or Firm* — Oblon, McClelland, Maier & Neustadt, L.L.P.

(57) ABSTRACT

According to an embodiment, in an X-ray diagnosis apparatus, a detector detects a position of a feature point in the sequentially generated X-ray images. A corrector performs a correction process such that an angle of a line segment including the feature point and a single point based on the feature point detected in any one of the sequentially generated X-ray images substantially agree with an angle based on the feature point and a single point based on the feature point detected in a new X-ray image generated after the X-ray image, thereby sequentially generating corrected images in which a position different from the feature point in the images is substantially the same. Every time each of the corrected images is newly generated by the corrector, a controller sequentially generates the corrected images, thereby displaying a moving image on a display unit.

20 Claims, 17 Drawing Sheets

(51) Int. Cl.
    *A61B 6/00*    (2006.01)
    *G06K 9/32*    (2006.01)

(56) References Cited

U.S. PATENT DOCUMENTS

| | | |
|---|---|---|
| 2008/0221442 A1 | 9/2008 | Tolkowsky et al. |
| 2008/0285824 A1* | 11/2008 | Wildes .................... A61B 8/12 382/128 |
| 2008/0287805 A1* | 11/2008 | Li ........................ A61B 8/0833 600/471 |
| 2010/0222671 A1 | 9/2010 | Cohen et al. |
| 2012/0230565 A1 | 9/2012 | Steinberg et al. |
| 2013/0303875 A1* | 11/2013 | Joy ...................... A61B 8/4416 600/407 |
| 2015/0282890 A1* | 10/2015 | Cohen .................. A61B 6/5288 600/424 |

\* cited by examiner

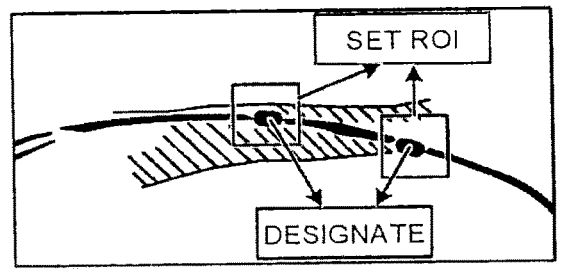
FIG. 3A
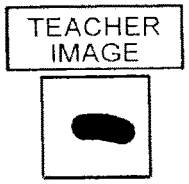
FIG. 3B
FIG. 4
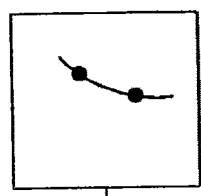 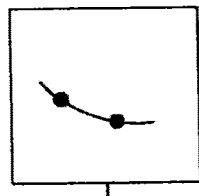
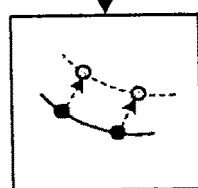 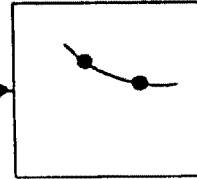

SINGLE-POINT FIXED DISPLAY
• MIDPOINT: (xs, ys)
• ANGLE: θs

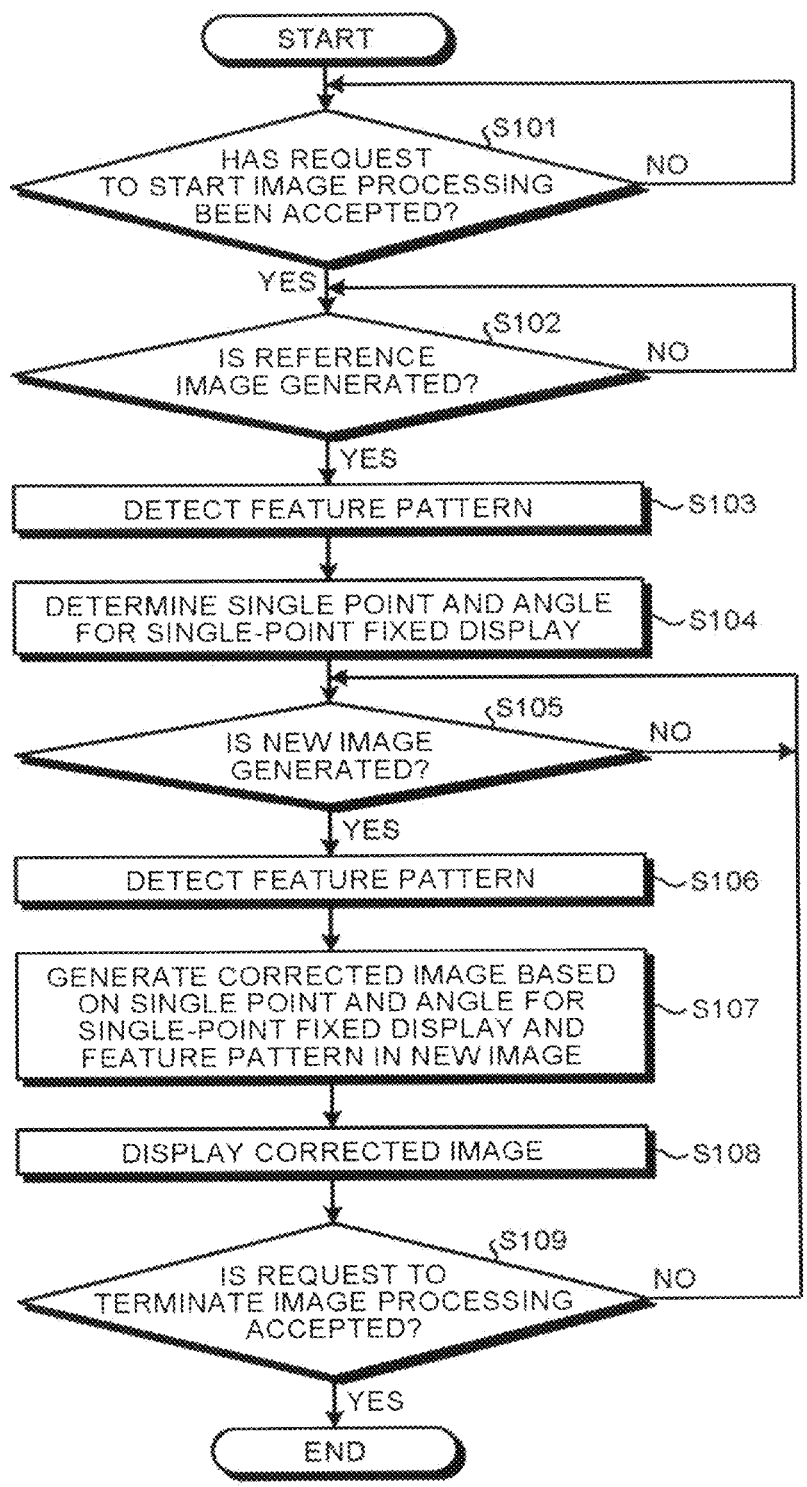

FIG.24
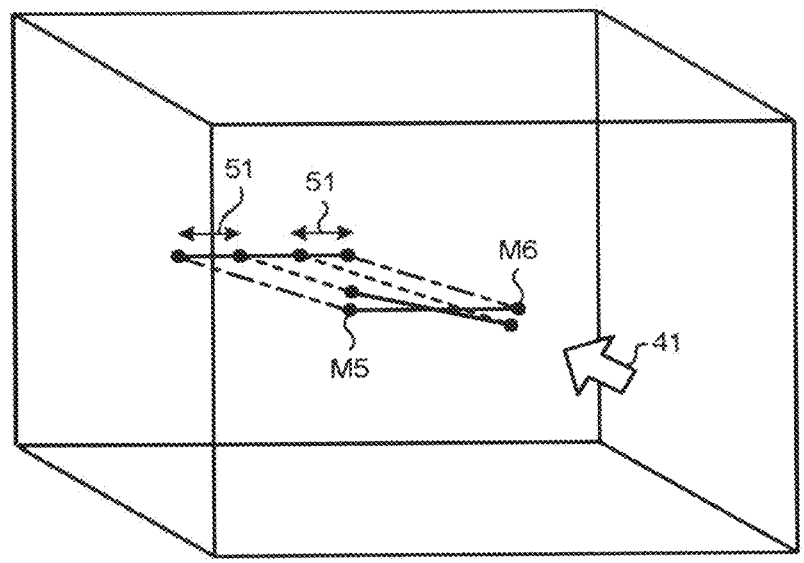
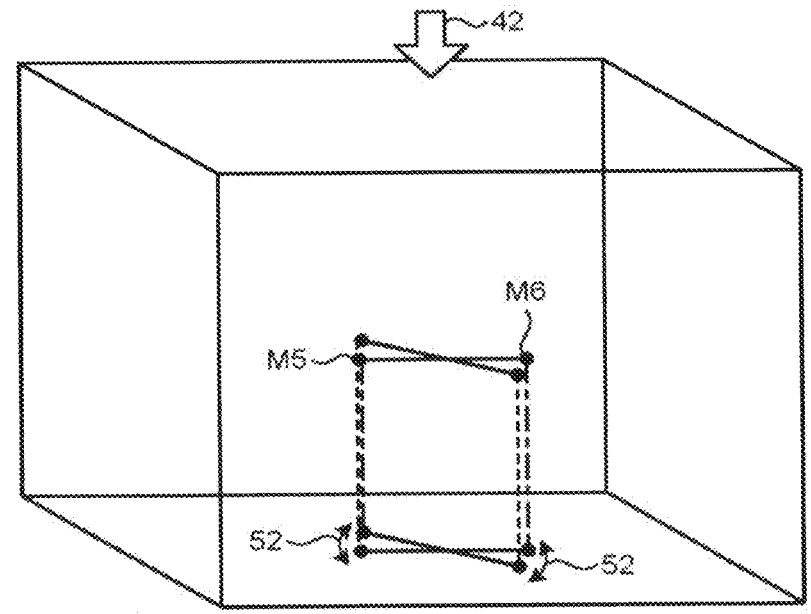

X-RAY DIAGNOSIS APPARATUS AND IMAGE PROCESSING APPARATUS

CROSS-REFERENCE TO RELATED APPLICATIONS

This application is based upon and claims the benefit of priority from Japanese Patent Application No. 2013-249550, filed on Dec. 2, 2013; the entire contents of which are incorporated herein by reference.

FIELD

Embodiments described herein relate generally to an X-ray diagnosis apparatus and an image processing apparatus.

BACKGROUND

Endovascular intervention treatment is treatment for treating a lesion in the heart, brain, liver, or other organs by inserting an instrument for treatment (device) called a catheter into a blood vessel. For example, in endovascular intervention treatment, a doctor inserts a balloon-tip catheter to a stenosis site. The doctor then, for example, injects fluid into the balloon through the catheter and inflates the balloon. The stenosis site is thereby inflated to restore the blood flow. The balloon-tip catheter is pulled out of the body by the doctor after the fluid in the balloon is sucked.

In order to prevent restenosis of the stenosis site inflated by the balloon, endovascular intervention treatment is conducted using a balloon-tip catheter having a metal mesh (stent strut) affixed to the outside of the balloon. In this treatment, the doctor inflates the stent strut by inflating the balloon and thereafter sucks the fluid in the balloon and pulls the catheter out of the body. The inflated stent strut is retained at the stenosis site, thereby reducing the possibility of restenosis at the stenosis site. The balloon-tip catheter having a stent strut is called a "stent".

In endovascular intervention treatment, it is necessary to move the device inserted into a blood vessel precisely to a treatment target site. In general, the device is positioned by referring to an X-ray image generated and displayed real-time by an X-ray diagnosis apparatus. For this purpose, the device has, for example, x-ray-opaque metal attached at two places (or one place) as markers indicating the position of the balloon or the stent. The doctor positions the device by referring to the markers visualized in the X-ray image appearing on the monitor.

However, when endovascular intervention treatment is conducted on a blood vessel in an organ such as the heart that always pulses or an organ that moves because of pulsation, the position of the device in the X-ray image always moves. It is therefore an extremely skillful task for doctors to position the device by referring to the X-ray image.

There is conventionally known a technique for displaying a moving image in which the device appears as if being substantially immobile, for example, by tracking the markers at two points visualized in the sequentially generated X-ray images and deforming the images such that the markers at two points in each X-ray image are located at the same positions as in the past image. A technique as a post-process is also known, which is for highlighting the device at a high contrast, for example, by obtaining the arithmetic mean of images of a plurality of frames in which the positions of the markers at two points are corrected to the same position.

However, the conventional techniques above do not necessarily assist in improving the accuracy in positioning the treatment device because image processing is applied such that the markers at two points are displayed at fixed positions.

BRIEF DESCRIPTION OF THE DRAWINGS

FIG. 3A and FIG. 3B are diagrams (1) for explaining a conventional technique;

FIG. 4 is a diagram (2) for explaining the conventional technique;

FIG. 14 is a flowchart for explaining an example of a process in an X-ray diagnosis apparatus according to the first embodiment;

FIG. 24 is a diagram for explaining an example of changing an imaging direction according to a sixth embodiment.

DETAILED DESCRIPTION

According to embodiment, a X-ray diagnosis apparatus comprising, an image generator, a detector, a corrector and a controller. The image generator that sequentially generates X-ray images based on X-rays emitted from an X-ray tube and transmitted through a subject. The detector that detects a position of a feature point in the sequentially generated X-ray images. The corrector that performs a correction process such that an angle of a line segment including the feature point and a single point based on the feature point detected in any one of the sequentially generated X-ray images substantially agree with an angle based on the feature point and a single point based on the feature point detected in a new X-ray image generated after the X-ray image, thereby sequentially generating corrected images in which a position different from the feature point in the images is located at substantially the same position. The controller that, every time each of the corrected images is newly generated by the corrector, sequentially displays the corrected images, thereby displaying a moving image on a display unit.

Embodiments of an X-ray diagnosis apparatus will be described in details below with reference to the accompanying drawings.

First Embodiment

Figure 1:
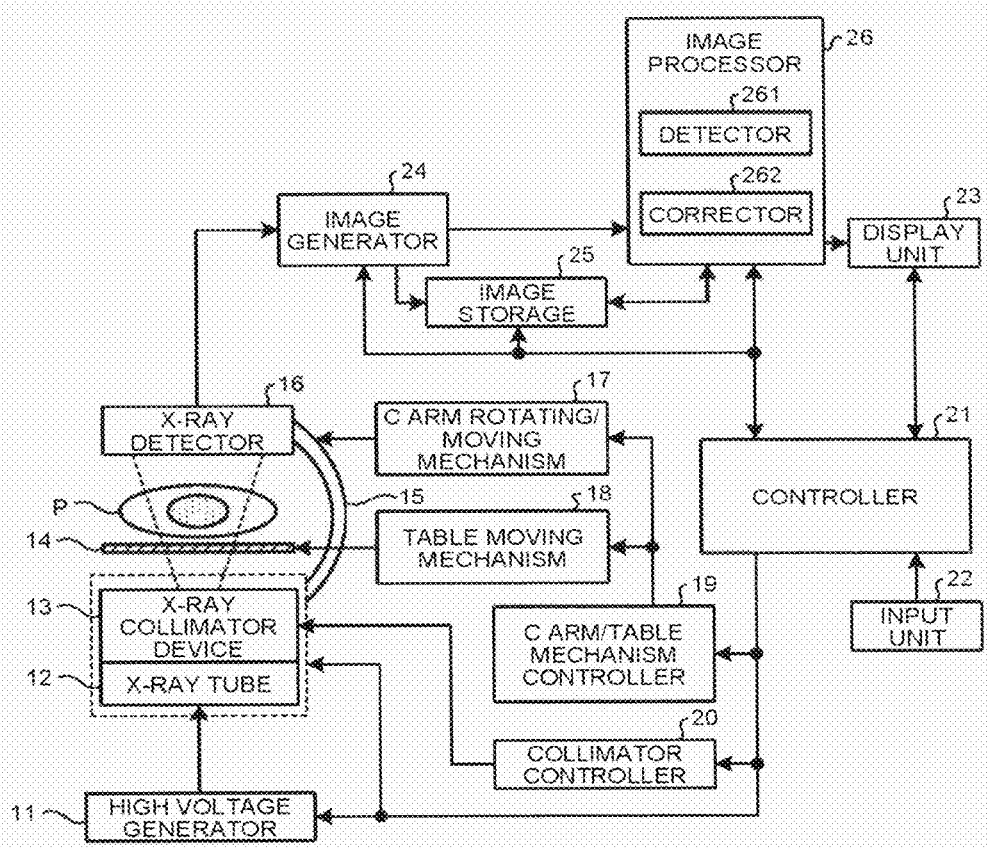
FIG. 1 is a block diagram illustrating a configuration example of an X-ray diagnosis apparatus according to a first embodiment.

First, a configuration of an X-ray diagnosis apparatus according to a first embodiment is described. FIG. 1 is a block diagram illustrating a configuration example of the X-ray diagnosis apparatus according to the first embodiment.

As illustrated in FIG. 1, the X-ray diagnosis apparatus according to the first embodiment includes a high voltage generator 11, an X-ray tube 12, an X-ray collimator device 13, a table 14, a C arm 15, an X-ray detector 16, a C arm rotating/moving mechanism 17, a table moving mechanism 18, a C arm/table mechanism controller 19, a collimator controller 20, a controller 21, an input unit 22, a display unit 23, an image generator 24, an image storage 25, and an image processor 26.

The high voltage generator 11 is a device that generates high voltage and supplies the generated high voltage to the X-ray tube 12. The X-ray tube 12 is a device that generates X-rays using the high voltage supplied from the high voltage generator 11. The high voltage generator 11 adjusts an X-ray dose applied to a subject P and controls ON/OFF of X-ray radiation to the subject P by adjusting the voltage supplied to the X-ray tube 12.

The X-ray collimator device 13 is a device for narrowing X-rays generated by the X-ray tube 12 such that they are selectively applied to a region of interest of the subject P. For example, the X-ray collimator device 13 has four slidable collimator blades, and the collimator blades are slid to narrow X-rays generated by the X-ray tube 12 and apply the narrowed X-rays to the subject P.

The table 14 is a bed on which the subject P lies, and is disposed on a couch (not illustrated).

The X-ray detector 16 detects X-rays transmitted through the subject P. For example, the X-ray detector 16 has detection elements arranged in a matrix. Each detection element converts X-rays transmitted through the subject P into an electrical signal, accumulates the thus converted electrical signals, and transmits the accumulated electrical signals to the image generator 24 described later.

The C arm 15 is an arm for holding the X-ray tube 12, the X-ray collimator device 13, and the X-ray detector 16. "The X-ray tube 12 and the X-ray collimator device 13" and the X-ray detector 16 are disposed so as to be opposed to each other by the C arm 15 with the subject P placed therebetween.

The C arm rotating/moving mechanism 17 is a mechanism for rotating and moving the C arm 15. The C arm rotating/moving mechanism 17 can change a source image receptor distance (SID) that is the distance between the X-ray tube 12 and the X-ray detector 16. The C arm rotating/moving mechanism 17 can also rotate the X-ray detector 16 held by the C arm 15.

The table moving mechanism 18 is a mechanism for moving the table 14. The C arm/table mechanism controller 19 adjusts the rotation and movement of the C arm 15 and the movement of the table 14 by controlling the C arm rotating/moving mechanism 17 and the table moving mechanism 18 under the control of the controller 21 described later. The collimator controller 20 controls a radiation range of X-rays applied to the subject P by adjusting the aperture of the collimator blades of the X-ray collimator device 13 under the control of the controller 21 described later.

The image generator 24 generates an X-ray image based on X-rays emitted from the X-ray tube 12 and transmitted through the subject. Specifically, the image generator 24 generates an X-ray image using the electrical signals converted from X-rays by the X-ray detector 16 and stores the generated X-ray image into the image storage 25. For example, the image generator 24 performs current/voltage conversion, A (analog)/D (digital) conversion, and parallel/serial conversion on the electrical signals received from the X-ray detector 16 and generates image data. In a fluoroscopy mode described later, the image generator 24 sequentially generates X-ray images based on X-rays emitted from the X-ray tube 12 and transmitted through the subject P.

The image storage 25 stores the X-ray images generated by the image generator 24.

The image processor 26 executes a variety of image processing on the X-ray image generated by the image generator 24. For example, the image processor 26 acquires an X-ray image directly from the image generator 24 and performs a variety of image processing. Otherwise, for example, the image processor 26 acquires an X-ray image generated by the image generator 24 from the image storage 25 and performs a variety of image processing. The image processor 26 can also store image data subjected to image processing into the image storage 25.

Here, as illustrated in FIG. 1, the image processor 26 according to the present embodiment has a detector 261 and a corrector 262. The image processing performed by the detector 261 and the corrector 262 illustrated in FIG. 1 will be described in detail later.

The input unit 22 is a control unit for an operator (for example, a doctor or a technician) to operate the X-ray diagnosis apparatus and accepts a variety of instructions from the operator. For example, the input unit 22 has a mouse, a keyboard, a button, a trackball, a joystick, and a footswitch. The input unit 22 transfers the instructions accepted from the operator to the controller 21 described later.

The display unit 23 has a monitor for displaying a graphical user interface (GUI) for accepting a command from the operator through the input unit 22 and for displaying an X-ray image generated by the image generator 24, an X-ray image subjected to image processing by the image processor 26, or other images. The display unit 23 may display image data output by the image generator 24 or the image processor 26 or may display image data acquired from the image storage 25.

The controller 21 controls the entire operation of the X-ray diagnosis apparatus. For example, the controller 21 controls the X-ray dose applied to the subject P and ON/OFF by controlling the high voltage generator 11 and adjusting the voltage supplied to the X-ray tube 12 in accordance with the operator's instruction transferred from the input unit 22. For example, the controller 21 adjusts the rotation and movement of the C arm 15 and the movement of the table 14 by controlling the C arm/table mechanism controller 19 in accordance with the operator's instruction. For example, the controller 21 controls the radiation range of X-rays applied to the subject P by controlling the collimator controller 20 and adjusting the aperture of the collimator blades of the X-ray collimator device 13 in accordance with the operator's instructions.

For example, the controller 21 controls the X-ray image generation process by the image generator 24 and the image processing by the image processor 26 in accordance with the operator's instructions. For example, the controller 21 performs control such that, for example, a GUI for accepting the operator's instructions and image data stored by the image storage 25 appear on the display unit 23.

Here, the X-ray diagnosis apparatus illustrated in FIG. 1 is an X-ray angiography system for use in diagnosis and treatment for the brain or the circulatory system such as the heart. The units that constitute the X-ray diagnosis apparatus illustrated in FIG. 1 are dispersively installed in the "procedure room" or "operating room" in which a procedure is carried out on the subject P and the "control room" in which the X-ray diagnosis apparatus is operated. For example, the high voltage generator 11, the X-ray tube 12, the X-ray collimator device 13, the table 14, the C arm 15, the X-ray detector 16, the C arm rotating/moving mechanism 17, the table moving mechanism 18, the C arm/table mechanism controller 19, and the collimator controller 20 are installed in the "procedure room" or operating room. For example, the controller 21, the image generator 24, the image storage 25, and the image processor 26 are installed in the control room.

Although the input unit 22 is illustrated as a single block in FIG. 1, a plurality of control units of the input unit 22 are dispersively installed in the procedure room (or operating room) and the control room. For example, the control units for giving an instruction to start generation and display of an X-ray image are installed both in the procedure room (or operating room) and in the control room. For example, the control units for giving an instruction to start image processing on an X-ray image are installed both in the procedure room (or operating room) and in the control room. For example, the control units for giving an instruction to rotate and move the C arm 15 are also installed both in the procedure room (or operating room) and in the control room.

Although the display unit 23 is illustrated as a single block in FIG. 1, the display unit 23 has a plurality of monitors, which are dispersively installed in the procedure room (or operating room) and the control room. For example, in the procedure room (or operating room), for example, an operating person who carries out a procedure observes an X-ray image or other images appearing on the monitor installed in the examination room. For example, in the control room, for example, the operator who operates the X-ray diagnosis apparatus in accordance with instructions from the operating person observes a variety of information appearing on the monitor installed in the control room.

The overall configuration of the X-ray diagnosis apparatus according to the first embodiment has been described above. In the first embodiment, the X-ray diagnosis apparatus having the foregoing configuration is used to perform endovascular intervention treatment for treating a lesion in the heart, brain, liver, or other organs by inserting an instrument for treatment (device) called a catheter into a blood vessel in the subject P.

For example, a doctor conducts endovascular intervention treatment using a "balloon-tip catheter having a stent strut" for a stenosis site in a blood vessel in the heart of the subject P. As an example, the doctor inserts a catheter into a blood vessel from a hole made in the skin of the femoral region and pushes the catheter to a stenosis site in the right coronary artery (RCA). In doing so, the doctor positions the device by referring to the X-ray image generated and displayed by the X-ray diagnosis apparatus.

Figure 2:
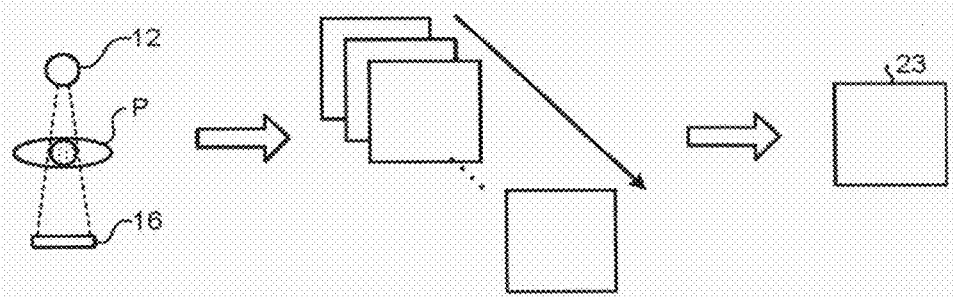
FIG. 2 is a diagram for explaining a fluoroscopy mode.
Figure 5:
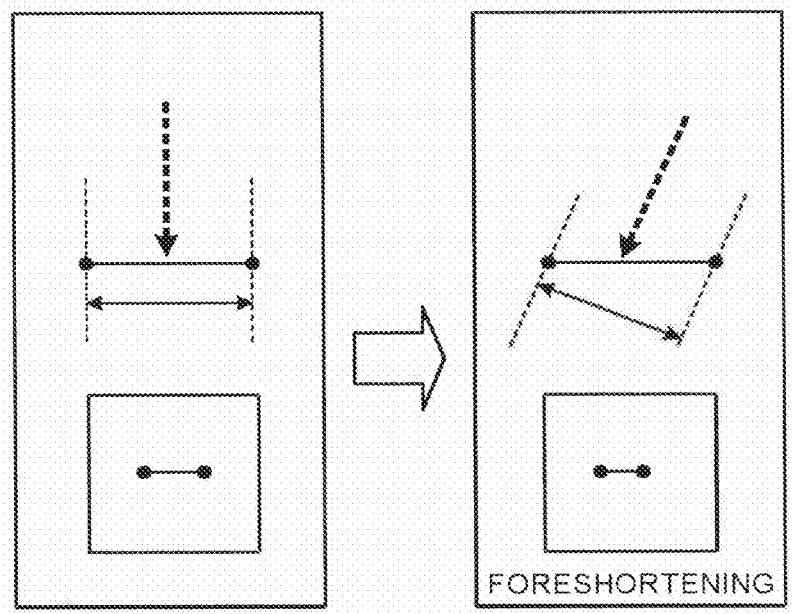
FIG. 5 is a diagram (1) for explaining problems of the conventional technique.

When endovascular intervention treatment is conducted, the X-ray diagnosis apparatus according to the first embodiment generates and displays an X-ray image in a fluoroscopy mode based on a command from the operator. In the fluoroscopy mode, X-ray images are sequentially generated with X-ray radiation, and the sequentially generated X-ray images appear real-time on the display unit 23. FIG. 2 is a diagram for explaining the fluoroscopy mode.

As illustrated in FIG. 2, the X-ray tube 12 emits X-rays to a region of interest (for example, heart) of the subject P, and the X-ray detector 16 sequentially detects X-rays transmitted through the region of interest. The image generator 24 then sequentially generates X-ray images in a time sequence based on the data sequentially detected by the X-ray detector 16, as illustrated in FIG. 2. Every time an X-ray image is newly generated, the display unit 23 updates the displayed image with the X-ray image newly generated, as illustrated in FIG. 2. In the fluoroscopy mode, X-ray images sequentially generated in a time sequence are thus displayed real-time as a moving image.

Here, for example, the device has x-ray-opaque metal attached at two places as markers indicating the position of the balloon or the stent. The doctor positions the device by referring to the markers visualized in the X-ray image appearing on the monitor.

However, when endovascular intervention treatment is conducted on a blood vessel in an organ such as the heart that always pulses or an organ that moves because of pulsation, the position of the device in the X-ray image always moves. It is therefore an extremely skillful task for doctors to position the device by referring to the X-ray image.

There is conventionally known a technique for displaying a moving image in which the device appears as if being substantially immobile, by tracking the markers at two points visualized in the sequentially generated X-ray images and deforming the images such that the markers at two points in each X-ray image are located at the same positions as in the past image. An example of the conventional technique is briefly described with reference to FIG. 3A, FIG. 3B, and FIG. 4. In the following description, it is assumed that the detector 261 and the corrector 262 of the image processor 26 illustrated in FIG. 1 are capable of executing the conventional technique. FIG. 3A, FIG. 3B, and FIG. 4 are diagrams for explaining the conventional technique.

The detector 261 detects a feature pattern of the instrument inserted into the subject P, in the X-ray images sequentially generated by the image generator 24. Every time the image generator 24 newly generates an X-ray image, the detector 261 detects the feature pattern in the newly generated X-ray image (hereinafter referred to as a new image). Specifically, the detector 261 detects the two markers in a new image and detects the positions (coordinates) of the two markers in the new image. Here, the above-described marker is marker indicating the position of the balloon or the stent, which is called "balloon marker" or "stent marker" (Hereinafter referred to as the stent marker).

For example, the controller 21 sets as a reference image an X-ray image (first frame) initially generated after an image processing request is accepted, and performs control such that the reference image appears on the monitor of the display unit 23, as illustrated in FIG. 3A. The doctor, referring to the first frame, designates the two stent markers in the first frame through the input unit 22, as illustrated in FIG. 3A. The detector 261 then detects the coordinates of each of the two stent markers in the first frame.

As illustrated in FIG. 3A, the detector 261 then sets as a region of interest (ROI) a rectangle centering on the coordinates of each of the two stent markers designated in the first frame, and extracts a pattern similar to the pattern in the set ROI from each of the sequentially generated new images, for example, by cross-correlation. For example, the detector 261 detects the center coordinates of the area in a new image that has the highest cross-correlation value to the ROI, as the coordinates of the stent marker.

The above-described process is only an example. For example, in the above-described process, the doctor may designate one of the stent markers. In this case, the detector 261 detects the coordinates of the other stent marker in the first frame as well by executing cross-correlation using the ROI set from the coordinates of the designated stent marker.

Alternatively, the process of tracking the two marker positions may be performed as follows. For example, the detector 261 detects the coordinates of the stent markers using a teacher image indicating the features such as the shape and the brightness in the X-ray image of the stent markers attached to the stent actually used in the treatment.

For example, as illustrated in FIG. 3B, the image storage 25 stores an X-ray image of the stent marker as a teacher image. The detector 261 then extracts a pattern similar to the teacher image, from X-ray images sequentially generated by the image generator 24, and searches for an area having the highest similarity among the extracted stent marker candidate areas. The detector 261 thus performs the process of tracking the two marker positions.

When the conventional technique is executed, the corrector 262 sequentially generates corrected images with the size, position, and inclination of the instrument being kept in the images, from the X-ray images sequentially generated by the image generator 24. For example, the corrector 262 sets the coordinates of the two stent markers detected by the detector 261 in the first frame, as reference coordinates. For example, the corrector 262 then generates corrected images by performing an image deformation process such that the coordinates of each of the two stent markers detected by the detector 261 in the new images in the second and subsequent frames agree with the reference coordinates. The image deformation process performed in the conventional technique is image processing including "translation, rotation, and rescale processes".

For example, the corrector 262 performs image deformation such that the positions of the two markers in the X-ray image in the n-th frame agree with the positions of the two markers in the X-ray image in the first frame, as illustrated in FIG. 4. The corrector 262 thus generates a corrected image (corrected image n) in the n-th frame from the X-ray image in the n-th frame, as illustrated in FIG. 4.

In the conventional technique, corrected images in which the two marker positions agree with the reference image are thus sequentially generated and displayed as a moving image on the display unit 23. However, the conventional technique above does not necessarily assist in improving the accuracy in positioning the instrument for treatment because image processing is applied for the purpose of fixedly displaying the markers at two points.

Specifically, in the conventional technique above, two problems described below occur. FIG. 5 to FIG. 8 are diagrams for explaining the problems of the conventional technique.

The first problem is that the conventional technique above does not allow the doctor to recognize "Foreshortening" of the device during endovascular treatment. For example, during the procedure targeting a blood vessel in the heart, the doctor observes the device from a plurality of directions by operating the C arm 15 and other units of the X-ray diagnosis apparatus.

However, depending on the X-ray radiation direction, the direction of the device and the X-ray radiation direction (X-ray imaging direction) may have a "right-angle relation (see the left diagram in FIG. 5)" or an "oblique relation (see the right diagram in FIG. 5)". In the case of the "oblique relation", a phenomenon (Foreshortening) occurs in which the length of the device looks short in a two-dimensional image obtained through normal imaging, as illustrated in the right diagram in FIG. 5.

Figure 6:
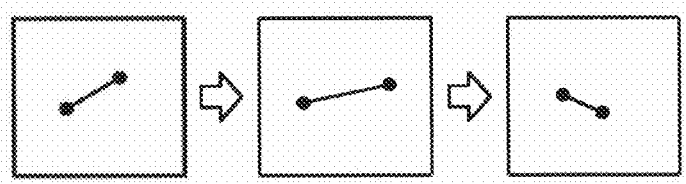
FIG. 6 is a diagram (2) for explaining the problems of the conventional technique.

In the case of the heart, with the "oblique relation", the device may appear to expand and contract in X-ray images with pulsing motion, as illustrated in FIG. 6. This point is described in detail. Here, even with the "oblique relation", if the motion of the device in connection with pulsing motion is only the movement in the front-to-back direction relative to the eye direction (X-ray radiation direction), the expansion and contraction of the device in the images is not observed. As illustrated in FIG. 6, it is when the degree of "oblique relation" changes with the pulsing motion that the expansion and contraction of the device is observed in the images. For example, in a case where the eye direction and the device direction have a "45-degree oblique" relation in diastole and the eye direction and the device direction have a "10-degree oblique" relation in systole, the device is observed as if it has contracted in the images.

Figure 7:
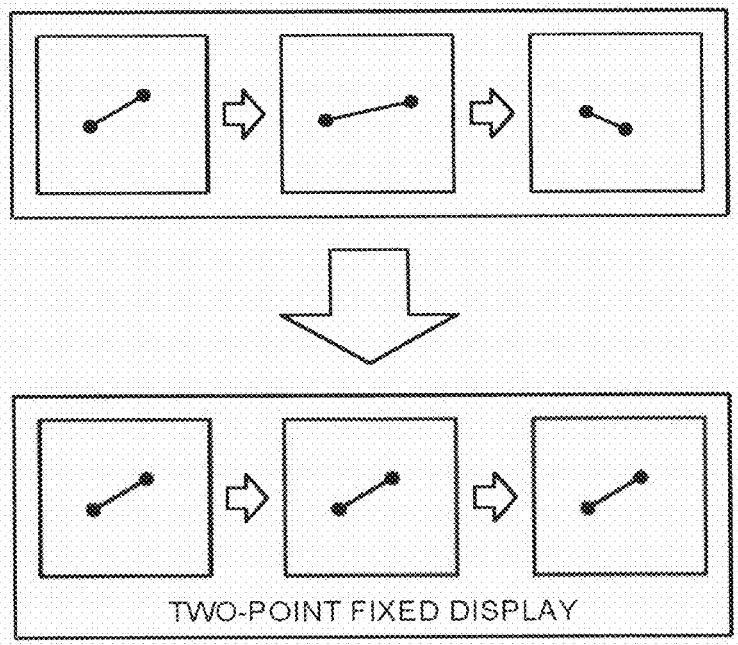
FIG. 7 is a diagram (3) for explaining the problems of the conventional technique.

However, in the above-described conventional technique, image processing is applied so as to fixedly display the marker positions at two points, based on the result of tracking the markers at two points. That is, when two-point fixed display is performed with the conventional technique, the device, which has appeared to expand and contract in a moving image of uncorrected X-ray images, appears at the same position, with the same inclination, and with the same size in a moving image of corrected images, as illustrated in FIG. 7.

In practice, therefore, even when "Foreshortening" occurs, the doctor cannot observe the expansion and contraction of the device even though referring to the corrected images processed for two-point fixed display. Consequently, the application of the conventional technique may result in reduction in the accuracy in positioning the device. In other words, if the conventional technique is not used, it is possible to perform a procedure while rotating the C arm 15 to observe the device in the optimum direction that does not cause "Foreshortening". However, if the conventional technique is used, the device is observed with approximately the same size even when "Foreshortening" occurs. Therefore, when using the conventional technique, the doctor proceeds to the task while observing the device in a direction that is not optimum and makes the observation difficult.

For example, if the device visualized in the reference image is in the most contracted state, a reduction process is performed so that the device is shortened in the corrected images sequentially generated and displayed from X-ray images. If the device is moved by referring to the moving image of those corrected images, the actual distance of movement differs from the distance of movement in the image. This phenomenon makes it difficult for the doctor to perform a procedure. Based on the foregoing, the conventional technique may reduce the accuracy in positioning the device.

Figure 8:
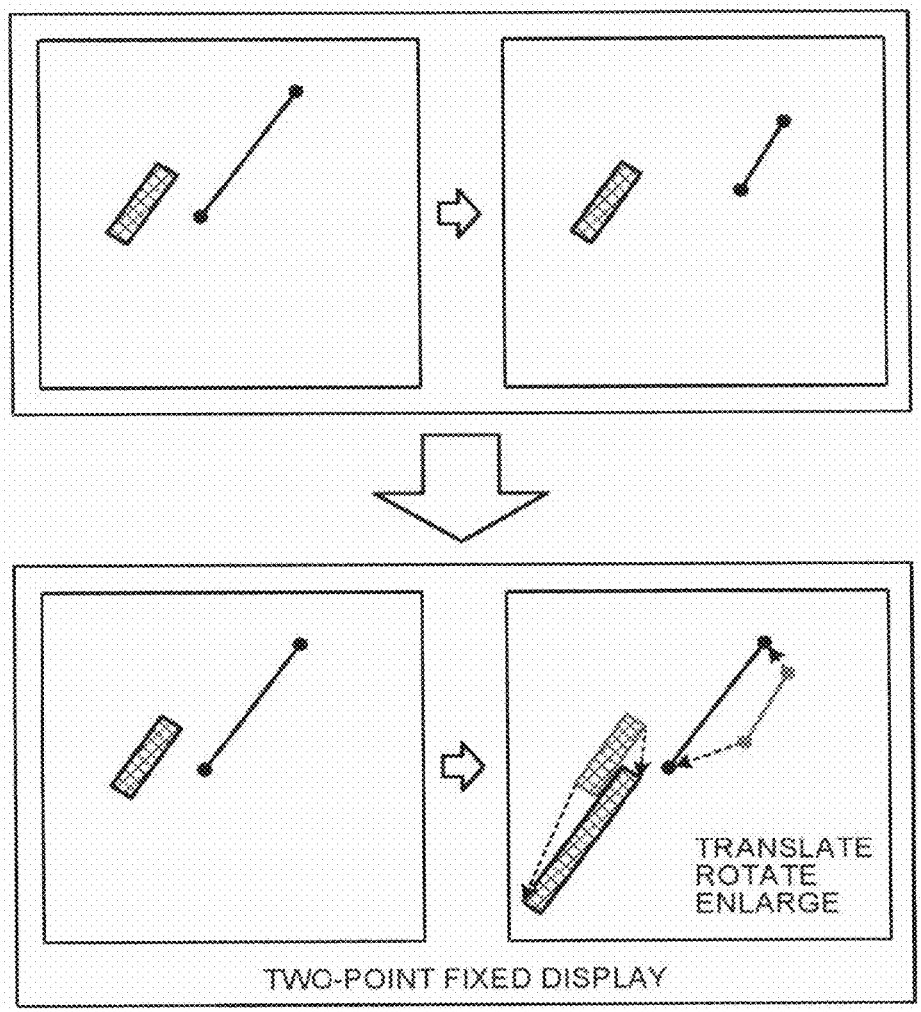
FIG. 8 is a diagram (4) for explaining the problems of the conventional technique.

The second problem is that the conventional technique causes the object surrounding the device to greatly expand and contract. As described above, in the conventional two-point fixed display, image processing is performed so that the distance between the markers at two points that expands and contracts due to pulsing motion is forced to be constant. That is, in the conventional two-point fixed display, the corrector 262 performs rescale together with translation and rotation, as illustrated in FIG. 8. In the corrected images, therefore, the background (for example, bone) other than the device greatly expands and contracts due to pulsing motion, as illustrated in FIG. 8.

However, if living tissues surrounding the device are used as an anatomical landmark during treatment, the expansion and contraction of the anatomical landmark makes it difficult to determine the position of the device. In addition, the rescale in the size of the surrounding object causes the entire image to vary, so that the doctor may find it difficult to observe the image or may easily become tired.

The image processor 26 according to the first embodiment then performs the following process as assistance for improving the accuracy in positioning the instrument for use in treatment.

The corrector 262 according to the first embodiment sequentially generates corrected images in which the positional relation between the instrument inserted in the subject P and a predetermined single point is kept in the images and the inclination of the instrument is kept at a predetermined angle, from the X-ray images sequentially generated by the image generator 24. In other words, in the first embodiment, the corrector 262 performs image deformation such that the size of the instrument visualized in the images is substantially constant between the uncorrected X-ray image and the corrected X-ray image while the position and inclination of the instrument visualized in the image is substantially constant among the sequentially generated corrected images.

More specifically, the corrector 262 according to the first embodiment generates a corrected image from an X-ray image to be corrected, by performing a translation process and/or a rotation process. The process performed by the corrector 262 according to the first embodiment does not include a rescale process. Here, the corrector 262 sequentially generates corrected images by performing the above-described correction process between images (frames) in X-ray images sequentially generated by the image generator 24. The X-ray diagnosis apparatus according to the present embodiment thus can generate and display a corrected image real-time.

Specifically, also in the first embodiment, the corrector 262 uses the tracking function of the detector 261. That is, the detector 261 according to the first embodiment detects the feature pattern of the instrument in the X-ray images sequentially generated by the image generator 24 as in the conventional technique. In other words, the detector 261 detects the positions of a feature point in the X-ray images sequentially generated by the image generator 24. For example, the detector 261 detects a stent marker through the process illustrated in FIG. 3A and FIG. 3B.

The corrector 262 then uses a single point and an angle defined from the feature pattern detected in the X-ray image (for example, the first frame) set as a reference image, as the predetermined single point and the predetermined angle described above. The corrector 262 then generates a corrected image from the target image, based on the feature pattern detected in the target image that is an X-ray image to be corrected, the predetermined single point, and the predetermined angle. That is, the corrector 262 performs a correction process such that the angle of a line segment including the feature point and a single point based on the feature point detected in any one of the X-ray images sequentially generated by the image generator 24 substantially agree with the angle based on the feature point and a single point based on the feature point detected in a new X-ray image generated after the X-ray image. In doing so, the corrector 262 sequentially generates corrected images in which a position different from the feature point in the images is located at substantially the same position. The controller 21 then causes the display unit 23 to display as a moving image the corrected images sequentially generated by the corrector 262.

In a case described below, a stent that is an instrument for treatment has two feature points (for example, two stent markers). In such a case, the detector 261 detects two feature points of the instrument as a feature pattern. The corrector 262 then uses a single point defined by the positions of the two feature points detected in a reference image, as a predetermined single point. The corrector 262 also uses the angle between the line segment connecting the two feature points detected in the reference image and a reference line in the reference image, as a predetermined angle. FIG. 9 to FIG. 12 are diagrams for explaining the corrector according to the first embodiment.

Figure 9:
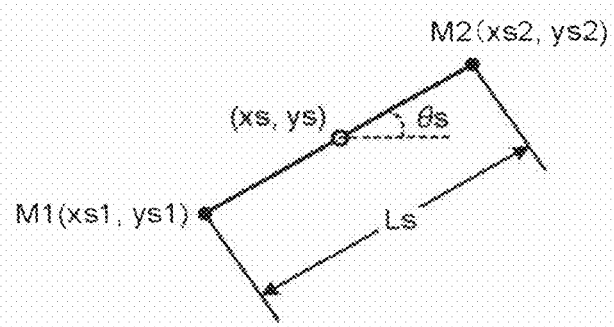
FIG. 9 is a diagram (1) for explaining a corrector according to the first embodiment.

For example, the detector 261 detects the position (coordinates) of each of the two markers (M1 and M2) in the X-ray image in the first frame set as a reference image. For example, the detector 261 detects "(xs1, ys1) and (xs2, ys2)" as the positions of M1 and M2, as illustrated in FIG. 9.

The corrector 262 determines the "position (coordinates) of a single point" for use in image deformation, from the detection result of the detector 261. For example, the corrector 262 calculates the center coordinates "(xs, ys)" between M1 and M2, as illustrated in FIG. 9. The center coordinates are the midpoint of the line segment (hereinafter called the line segment M1&2) connecting M1 and M2. That is, "xs" is given by "(xs1+xs2)/2" and "ys" is given by "(ys1+ys2)/2". The corrector 262 further calculates the angle "θs" between the line segment M1&2 and the reference line extending horizontally in the reference image, for example, as illustrated in FIG. 9.

The controller 21 may calculate "(xs, ys)" and "θs". An X-ray image used as the reference image may be an X-ray image in a frame (for example, the fifth frame) other than the first frame. An X-ray image used as the reference image may be the first X-ray image that has the cross correlation value greater than a predetermined threshold.

The "single point and angle" for use in the image deformation process performed in the first embodiment are thus defined, and the detector 261 subsequently detects the positions (coordinates) of M1 and M2 in an X-ray image (target image) to be corrected, which is generated after the reference image. The corrector 262 then deforms the target image such that the position (coordinates) of the midpoint of the line segment M1&2 in the target image agrees with (xs, ys) and such that the angle between the line segment M1&2 and the reference line agrees with "θs", as illustrated in FIG. 10.

That is, in the first embodiment, the target image is deformed such that the device visualized in the corrected images passes through the same single point and such that the device visualized in the corrected images inclines at the same angle. The controller 21 then causes the display unit 23 to display as a moving image the corrected images sequentially generated by the corrector 262.

Figure 10:
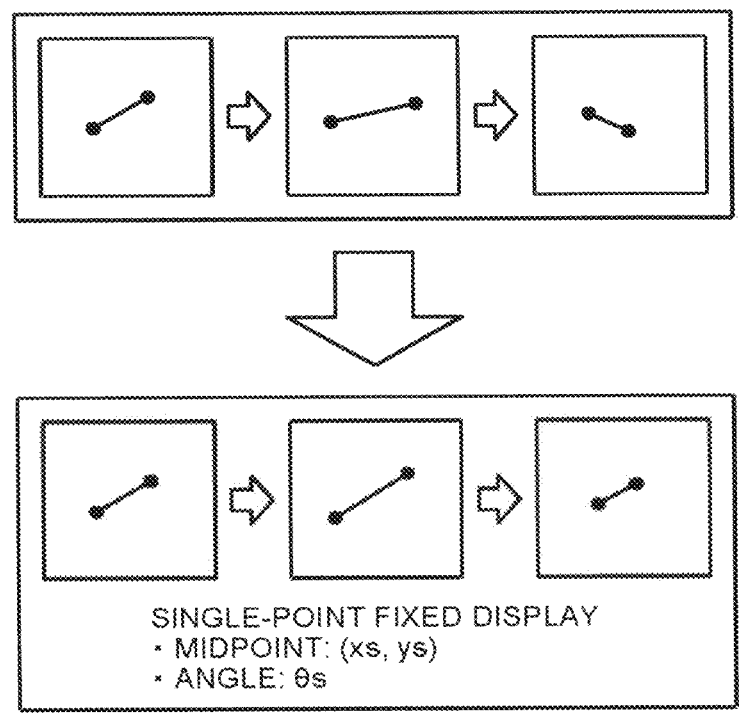
FIG. 10 is a diagram (2) for explaining the corrector according to the first embodiment.

In other words, the moving-image display performed in the first embodiment is "single-point fixed display" as illustrated in FIG. 10. In the single-point fixed display, the device is displayed at approximately the same position and with approximately the same inclination, so that the visibility of the device is improved as in the conventional two-point fixed display.

Figure 11:
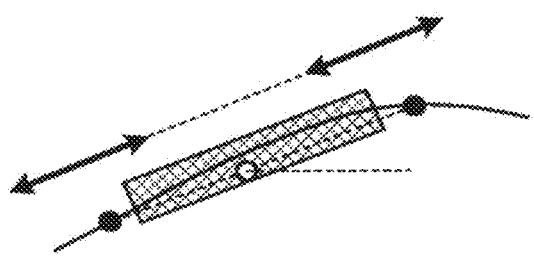
FIG. 11 is a diagram (3) for explaining the corrector according to the first embodiment.

However, in the single-point fixed display, if the direction of the device and the X-ray radiation direction (X-ray imaging direction) have the "oblique relation" and the degree of the "oblique relation" changes, the distance ("Ls" illustrated in FIG. 9) between the markers in the reference image varies among the corrected images. That is, in the single-point fixed display, the distance between the two markers may expand or contract with respect to the white circle at the center coordinates (xs, ys), as illustrated in FIG. 11. In other words, in the single-point fixed display, while the visibility of the device is ensured, the occurrence of "Foreshortening" can be recognized. Specifically, in the single-point fixed display, the occurrence of "Foreshortening" can be recognized in a state where the degree of the "oblique relation" changes.

Figure 12:
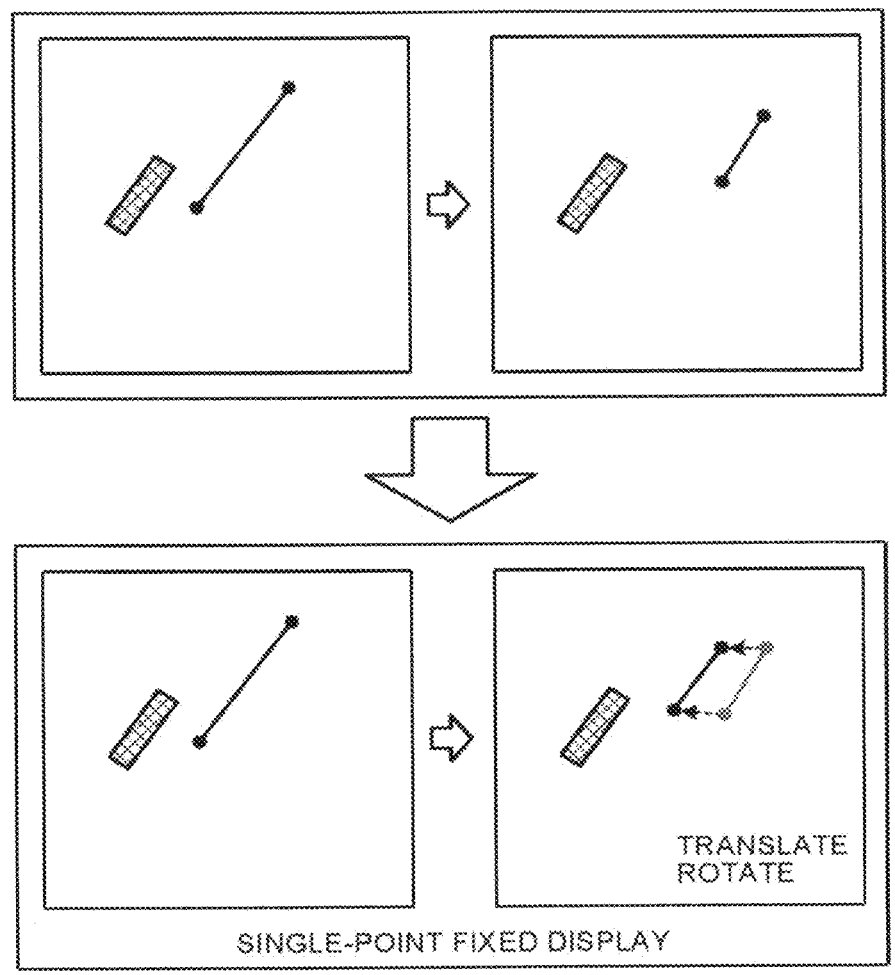
FIG. 12 is a diagram (4) for explaining the corrector according to the first embodiment.

Since the image deformation performed in the single-point fixed display is translation and/or rotation, as illustrated in FIG. 12, the size of an object located around the device does not change before and after image deformation. The single-point fixed display therefore allows the doctor to easily determine the position of the device even when the living tissues surrounding the device are used as an anatomical landmark during treatment.

In the foregoing description, the single point for use in single-point fixed display is the midpoint of the line segment M1&2 in the reference image. However, the single point for use in single-point fixed display may be M1 or M2 in the reference image. Specifically, the corrector 262 performs a correction process such that the angle of a line segment including the feature point and a single point of the feature point detected in any one of the X-ray images sequentially generated by the image generator 24 substantially agree with the angle based on the feature point and a single point of the feature point detected in a new X-ray image generated after the X-ray image. In doing so, the corrector 262 sequentially generates corrected images in which a position different from the feature point in the images is located at substantially the same position. For example, the corrector 262 performs image deformation such that the position of M1 or M2) detected in the target image agrees with the position of M1 (or M2) in the reference image.

Alternatively, the corrector 262 may use a preset single point as the single point for use in single-point fixed display. For example, the corrector 262 may use, as the single point for use in single-point fixed display, the center coordinates of an area in which a corrected image is displayed. In such a case, the corrector 262 performs image deformation, for example, such that the position of M1 detected in the target image, the position of M2 detected in the target image, or the position of the midpoint of the line segment M1&2 in the target image agrees with the center coordinates of the corrected image display area.

The operator of the X-ray diagnosis apparatus can change the condition for setting the single point for use in single-point fixed display to any desired condition.

Figure 13A:
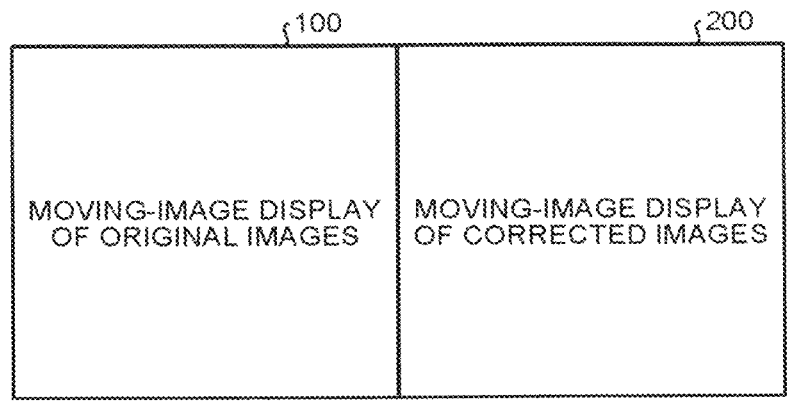
FIG. 13A to FIG. 13C are diagrams for explaining moving-image display manners according to the first embodiment.
Figure 13B:
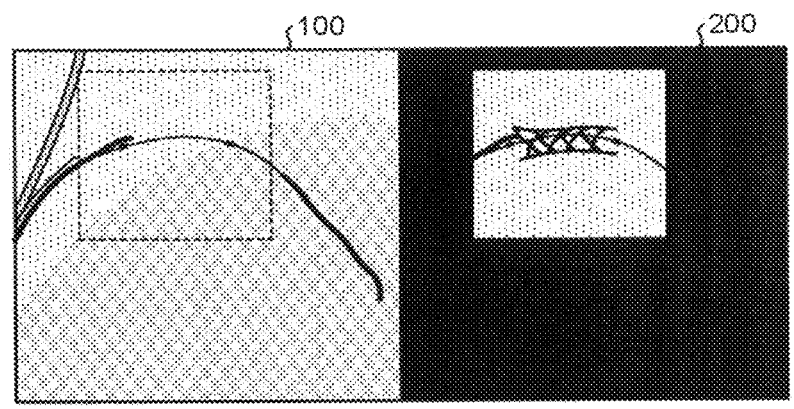
Figure 13C:
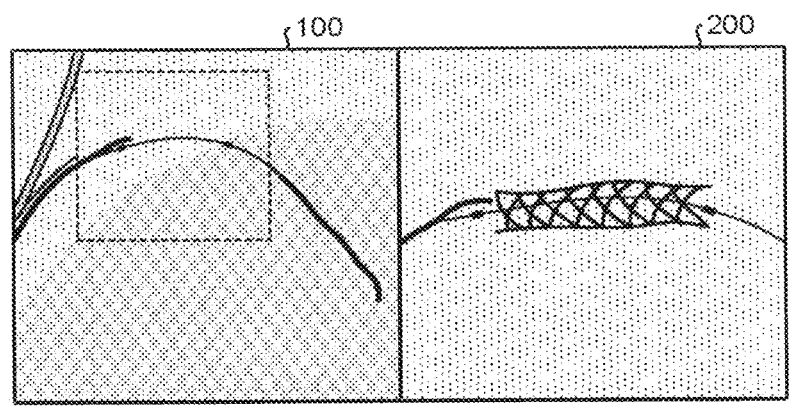

The controller 21 according to the first embodiment, which controls moving-image display of corrected images, may additionally perform display control as follows. FIG. 13A to FIG. 13C are diagrams for explaining moving-image display manners according to the first embodiment.

For example, the controller 21 performs control for displaying corrected images as a moving image as well as control for displaying, as a moving image, X-ray images sequentially generated by the image generator 24. In FIG. 13A, uncorrected X-ray images (original images) are displayed as a moving image in a display area 100, and corrected images are displayed as a moving image in a display area 200. In such a case, the controller 21 allows X-ray images sequentially generated by the image generator 24 to sequentially appear in the display area 100 and allows corrected images sequentially generated by the corrector 262 to sequentially appear in the display area 200.

The display area 100 and the display area 200 may be set in a single monitor of the display unit 23 or may be set in two monitors of the display unit 23.

Alternatively, the controller 21 performs control for displaying, as a moving image, a predetermined area including the instrument in the corrected image. For example, the controller 21 sets a rectangular area of the same size including a single point for single-point fixed display in a corrected image, as a display target. The controller 21 then executes moving-image display of original images in the display area 100 and executes moving-image display of the rectangular area cut out from the corrected images in the display area 200, as illustrated in FIG. 13B.

Alternatively, the controller 21 performs control for displaying, as a moving image, enlarged images in which the predetermined area is enlarged. For example, the controller 21 displays original images as a moving image in the display area 100 and displays, as a moving image, the enlarged images in the display area 200 in which the rectangular area is enlarged up to the size of the display area 200, as illustrated in FIG. 13C. The controller 21 may further execute moving-image display by adding a "frame" at a position in the original image of the display area 100 that corresponds to the rectangular area displayed in the form of a moving image as corrected images, as illustrated in FIG. 13B and FIG. 13C.

The above-described display manners allow an observer of the display unit 23 to compare the images before and after correction. When the display manner as in FIG. 13B or FIG. 13C is performed, the moving-image display of the original images may not be executed.

Referring now to FIG. 14, the process in the X-ray diagnosis apparatus according to the first embodiment is described. FIG. 14 is a flowchart for explaining an example of the process in the X-ray diagnosis apparatus according to the first embodiment. In connection with FIG. 14, an example of the process after starting the fluoroscopy mode of sequentially generating X-ray images of the subject P with a catheter inserted therein is explained.

As illustrated in FIG. 14, the controller 21 of the X-ray diagnosis apparatus according to the first embodiment determines whether a request to start image processing for single-point fixed display has been accepted (step S101). Here, if a request to start image processing has not been accepted (No at step S101), the controller 21 waits until a request to start image processing is accepted.

On the other hand, if a request to start image processing has been accepted (Yes at step S101), the controller 21 determines whether a reference image (the first frame) has been generated (step S102). Here, if a reference image has not been generated (No at step S102), the controller 21 waits until a reference image is generated.

On the other hand, if a reference image has been generated (Yes at step S102), the detector 261 detects a feature pattern in the reference image under the instruction from the controller 21 (step S103). In the first embodiment, the detector 261 detects the positions of two stent markers in the reference image.

The corrector 262 then determines a single point and an angle for single-point fixed display under the instruction from the controller 21 (step S104, see FIG. 9). The detector 261 then determines whether a new image (an X-ray image to be corrected, a target image) has been generated, under the instruction from the controller 21 (step S105). Here, if a new image has not been generated (No at step S105), the detector 261 waits until a new image is generated.

On the other hand, if a new image has been generated (Yes at step S105), the detector 261 detects a feature pattern in the new image (step S106). In the first embodiment, the detector 261 detects the positions of two stent markers in the new image.

The corrector 262 then generates a corrected image based on the single point and the angle for single-point fixed display and the feature pattern in the new image (step S107).

The display unit 23 then displays the corrected image generated at step S107 (step S108). The display unit 23 may perform moving-image display illustrated in FIG. 13A and FIG. 13B, at step S108.

The controller 21 then determines whether a request to terminate image processing has been accepted (step S109). Here, if a request to terminate image processing has not been accepted (No at step S109), the controller 21 returns to step S105 and determines whether a new image has been generated.

On the other hand, if a request to terminate image processing has been accepted (Yes at step S109), the controller 21 terminates the image processing.

As described above, in the first embodiment, the corrector 262 generates a corrected image from a new image (an X-ray image to be corrected), based on the marker tracking result from the detector 261. Specifically, in the first embodiment, the corrector 262 generates corrected images such that the instrument visualized in the respective images after image deformation passes through approximately the same single point and such that the instrument visualized in the respective images after image deformation inclines approximately at the same angle. In the first embodiment, the display unit 23 then displays the corrected images as a moving image.

In such single-point fixed display, while the visibility of the instrument is ensured, the occurrence of "Foreshortening" can be recognized. Since the image deformation performed in single-point fixed display is translation and/or rotation, the sizes of the instrument and an object located around the instrument do not change. That is, in single-point fixed display, when moving the instrument, the doctor can feel that the distance of actual movement and the distance of movement in the image are approximately the same. Based on the foregoing, the first embodiment can provide assistance for improving the accuracy in positioning the instrument for use in treatment.

Modification

Figure 15:
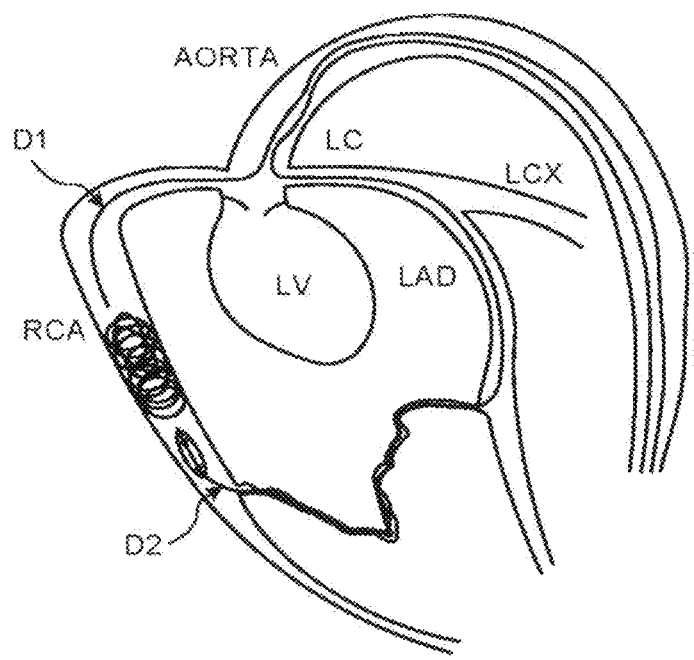
FIG. 15 is a diagram (1) for explaining a modification of the first embodiment.
Figure 16:
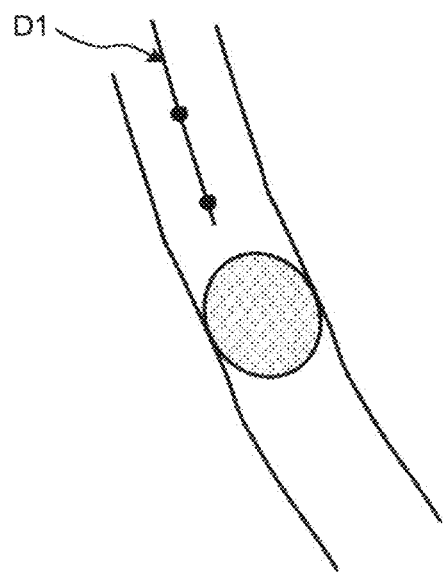
FIG. 16 is a diagram (2) for explaining the modification of the first embodiment.

The single-point fixed display described in the first embodiment above can be applied to a procedure described below in addition to the procedure of inflating a stenosis site. Such a modification is described with reference to FIG. 15 and FIG. 16. FIG. 15 and FIG. 16 are diagrams for explaining a modification of the first embodiment.

FIG. 15 illustrates a coronary artery, which is an artery that arises from the sinus of Valsalva of the aorta and supplies oxygen to the myocardium, as well as the left ventricle (LV). As illustrated in FIG. 15, the coronary artery branches into the right coronary artery (RCA) and the left coronary artery (LC) in such a manner as to surround the heart. The left coronary artery further branches into the left circumflex (LCX) and the left anterior descending (LAD).

In FIG. 15, part of the RCA is occluded substantially completely by a thrombus and a new blood vessel is formed from the LAD to the RCA through vascularization in order to supply oxygen to the territory of the RCA. In such a case, in order to remove the thrombus, a doctor inserts a device D1 and a device D2 so as to sandwich the Occlusion site, as illustrated in FIG. 15. In FIG. 15, the device D1 is inserted into the RCA from the aorta so as to be located above the Occlusion site. In FIG. 15, the device D2 is inserted from the aorta and passes through the LC, the LAD, and the new blood vessel so as to be located below the Occlusion site.

Here, the device D1 is a wire inserted through a catheter. The doctor uses the wire, that is, the device D1 to remove the thrombus that forms the Occlusion site. The device D2 is a balloon-tip guide wire inserted through a catheter and has two balloon markers indicating the position of the balloon, as illustrated in FIG. 15. The doctor can also use the guide wire that is the device D2, together with the device D1 to remove the thrombus that forms the Occlusion site.

In performing such a procedure, the doctor uses the device D2 as a landmark for positioning the device D1. Specifically, the doctor inflates the balloon as illustrated in FIG. 15 to enhance the visibility of the device D2 and observes the two balloon markers visualized in the X-ray image.

However, in the case of the procedure illustrated in FIG. 15, with the conventional two-point fixed display, image deformation is performed such that the positions of the two balloon markers of the device D2 are the same among the corrected images. In such a case, the position and size in the corrected images of the device D1 located away from the device D2 varies greatly with pulsing motion. The accuracy in positioning the device D1 is therefore reduced in the conventional two-point fixed display.

On the other hand, in the case of the procedure illustrated in FIG. 15, if the above-described single-point fixed display is applied, the positional relation between the device D1 and the device D2 is the same before and after image deformation and the size of the device D1 is the same before and after image deformation. The single-point fixed display therefore can improve the accuracy in positioning the device D1.

The Occlusion site may be removed using the device D1 alone. In such a case, as illustrated in FIG. 16, the single-point fixed display can be applied by using a device D1 having two markers attached to a wire. Also in such a case, it is possible to assist in improving the accuracy in positioning the device D1.

Second Embodiment

Figure 17:
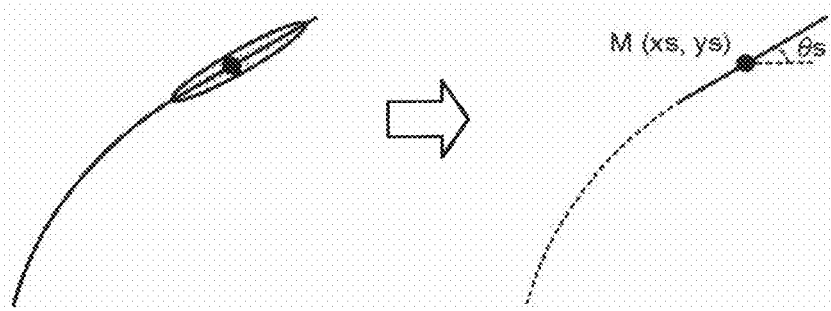
FIG. 17 is a diagram for explaining a second embodiment.

In a second embodiment, the process of performing single-point fixed display with an instrument for use in treatment having a single marker is described with reference to FIG. 17. FIG. 17 is a diagram for explaining the second embodiment.

The X-ray diagnosis apparatus according to the second embodiment is configured in the same manner as the X-ray diagnosis apparatus according to the first embodiment illustrated in FIG. 1. However, the detector 261 according to the second embodiment detects a single feature point of the instrument and a linear feature line of the instrument, as a feature pattern. The corrector 262 according to the second embodiment then uses a single point defined by the position of the single feature point detected in the reference image, as a single point for single-point fixed display. The corrector 262 according to the second embodiment then uses the angle between the feature line detected in the reference image and the reference line in the reference image, as the angle for single-point fixed display.

The left diagram in FIG. 17 illustrates a balloon-tip guide wire inserted through a catheter. The left diagram in FIG. 17 illustrates a guide wire having a single balloon marker indicating the position of the balloon.

In such a case, the detector 261 detects the coordinates "(xs, ys)" of the balloon marker M, which represents a single point in the reference image, as illustrated in the right diagram in FIG. 17. The corrector 262 determines the position at the coordinates "(xs, ys)" as the position of the single point for single-point fixed display.

The detector 261 detects a line passing through the balloon marker M in the reference image. Here, if the detector 261 detects a straight line passing through the balloon marker M in the reference image, the corrector 262 calculates the angle "θs" between the straight line and the reference line (a horizontal line) as the angle for single-point fixed display, as illustrated in the right diagram in FIG. 17. If a curve passing through the balloon marker M is detected in the reference image, the detector 261 further detects the tangent to the curve at the coordinates "(xs, ys)". The corrector 262 then calculates the angle between the tangent and the reference line as the angle for single-point fixed display.

Every time a target image is sequentially generated, the detector 261 detects the coordinates of the balloon marker M and the feature line passing through the balloon marker M in the target image. The corrector 262 then generates a corrected image by deforming the target image such that the coordinates of the balloon marker M are "(xs, ys)" and such that the inclination of the feature line is "θs", and outputs the corrected image to the display unit 23.

Also in the second embodiment, the position of the single point for single-point fixed display may be set at a preset single point in the same manner as in the first embodiment. For example, also in the second embodiment, the position of the single point for single-point fixed display may also be the center position of the display area 200. In such a case, the corrector 262 deforms the target image such that the coordinates of the balloon marker M correspond to the center position of the display area 200.

The explanation in the first embodiment is applicable to the second embodiment except that a corrected image is generated using a marker at a single point and a feature line.

As described above, the second embodiment can provide single-point fixed display that can improve the accuracy in positioning the device even when treatment is conducted using a device having a single marker.

Third Embodiment

Figure 18A:
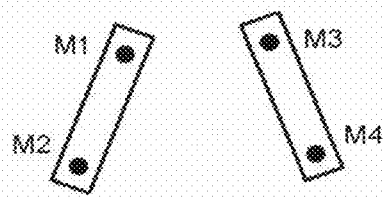
FIG. 18A to FIG. 18C are diagrams for explaining a third embodiment.
Figure 18B:
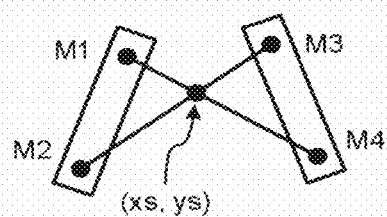

In a third embodiment, the process of performing single-point fixed display with an instrument for use in treatment having three or more markers is described with reference to FIG. 18A and FIG. 18B. FIG. 18A and FIG. 18B are diagrams for explaining the third embodiment.

The X-ray diagnosis apparatus according to the third embodiment is configured in the same manner as the X-ray diagnosis apparatus according to the first embodiment illustrated in FIG. 1. However, the detector 261 according to the third embodiment detects at least three feature points of an instrument or a plurality of instruments, as a feature pattern. The corrector 262 according to the third embodiment then uses a single point defined by at least one of the at least three feature points detected in a reference image, as a single point for single-point fixed display. The corrector 262 according to the third embodiment uses the angle between the line connecting at least two of the at least three feature points detected in the reference image and a reference line in the reference image, as the angle for single-point fixed display.

FIG. 18A illustrates a case where two devices each having two stent markers are inserted into two blood vessels close to each other in the subject P. In FIG. 18A, two stent markers of one of the devices are denoted by M1 and M2 and two stent markers of the other device are denoted by M3 and M4.

In such a case, the detector 261 detects the coordinates of the marker M1, the coordinates of the marker M2, the coordinates of the marker M3, and the coordinates of the marker M4, in the reference image. The detector 261 distinguishes M1 and M2 from M3 and M4, for example, with the doctor designating them in the reference image or by detecting a guide wire or mesh.

The corrector 262 then obtains the point of intersection between a line segment M1&4 connecting M1 and M4 and a line segment M2&3 connecting M2 and M3, for example, as illustrated in FIG. 18B. The corrector 262 then determines the coordinates "(xs, ys)" of the point of intersection in the reference image as the position of a single point for single-point fixed display, for example, as illustrated in FIG. 18B. Alternatively, the corrector 262 may determine the coordinates of the midpoint of the line segment M2&3 as the coordinates "(xs, ys)" of a single point for single-point fixed display.

Figure 18C:
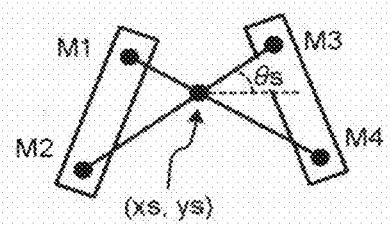

The corrector 262 calculates the angle "θs" between the line segment M2&3 connecting M2 and M3 and the reference line (a horizontal line) passing through the point of intersection (xs, ys) in the reference image, as the angle for single-point fixed display, for example, as illustrated in FIG. 18C.

Every time a target image is sequentially generated, the detector 261 detects the coordinates of the balloon markers M1 to M4 in the target image. The corrector 262 then generates a corrected image by deforming the target image such that the coordinates of the point of intersection between the line segment M1&4 and the line segment M2&3 agree with "(xs, ys)" and the angle between the line segment M2&3 and the reference line agrees with "θs", and outputs the corrected image to the display unit 23.

In the third embodiment, the position of the single point and the angle for use in single-point fixed display are not limited to the example illustrated in FIG. 18B and FIG. 18C. The position of the single point for use in single-point fixed display may be set, for example, at any one of M1 to M4 detected in the reference image. The angle for use in single-point fixed display may be set to the angle between the reference line and any one of the line segment connecting M1 and M2, the line segment connecting M1 and M3, the line segment connecting M2 and M4, and the line segment connecting M3 and M4.

For example, the corrector 262 may deform the target image such that the coordinates of M1 in the target image agree with the coordinates of M1 in the reference image and such that the angle between the line segment M1&2 and the reference line in the target image agrees with the angle between the line segment M1&2 and the reference line in the reference image.

Also in the third embodiment, the position of the single point for single-point fixed display may be set at a preset single point. For example, also in the third embodiment, the position of the single point for single-point fixed display may be the center position of the display area 200. In such a case, for example, the corrector 262 deforms the target image such that the coordinates of any one of M1 to M4 or the coordinates of the point of intersection between the line segment M1&2 and the line segment M3&4 correspond to the center of the display area 200.

The explanation in the first embodiment is applicable to the third embodiment except that a corrected image is generated using markers at three or more points.

As described above, the third embodiment can provide single-point fixed display that can improve the accuracy in positioning the device even when treatment is conducted using a device having three or more markers.

Fourth Embodiment

Figure 19A:
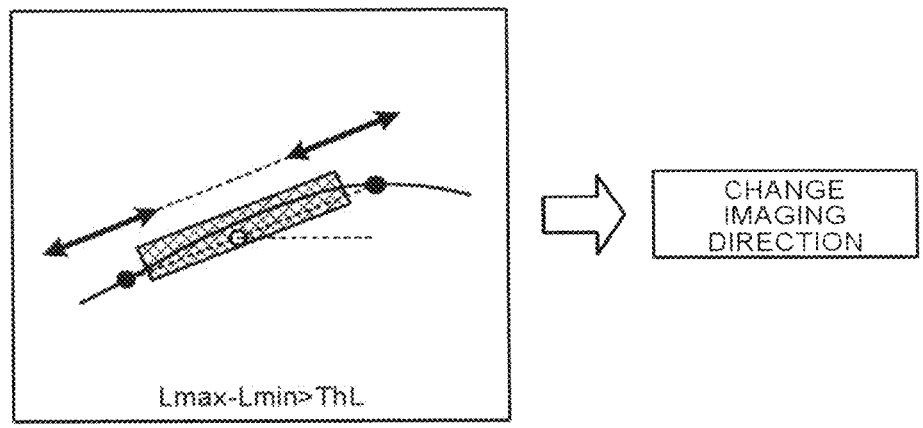
FIG. 19A and FIG. 19B are diagrams for explaining a fourth embodiment.
Figure 19B:
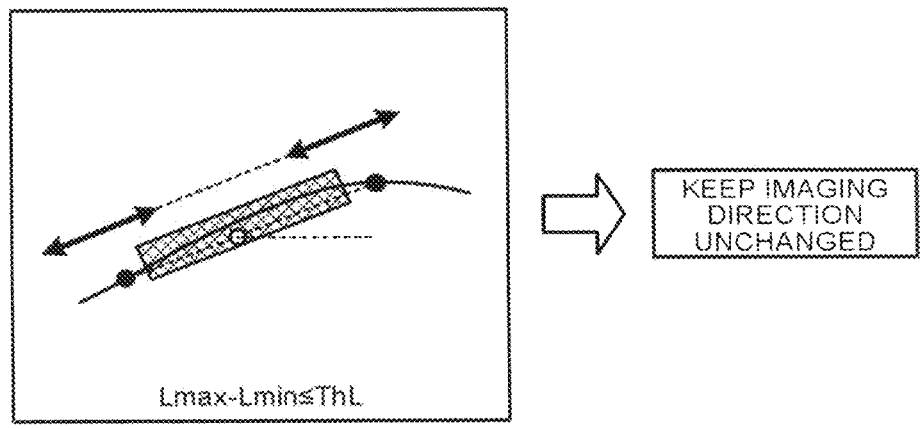

In a fourth embodiment, whether "Foreshortening" occurs is automatically detected in a state where single-point fixed display is being performed, and the operator is notified of the detection result. This case is described with reference to, for example, FIG. 19A and FIG. 19B. FIG. 19A and FIG. 19B are diagrams for explaining the fourth embodiment.

In the single-point fixed display described in the first to the third embodiments, the operator can recognize the occurrence of "Foreshortening" from variation in size of the instrument in corrected images. Specifically, in the single-point fixed display, the operator can recognize the occurrence of "Foreshortening" in a state where the degree of the "oblique relation" changes. Here, the amount of variation in size of the instrument in corrected images can be acquired from the detection result of the detector 261. In the single-point fixed display, the amount of variation in size of the instrument in corrected images is equal to the amount of variation in size of the instrument in the original images.

The controller 21 according to the fourth embodiment determines whether the size of the instrument visualized in the corrected images sequentially generated by the corrector 262 falls within a predetermined range or outside the range. The controller 21 according to the fourth embodiment then notifies the operator of the determination result.

Specifically, if the size of the instrument visualized in the corrected images sequentially generated by the corrector 262 varies outside the predetermined range, the controller 21 gives a notice to prompt the operator to change the X-ray radiation direction to the subject P. If the size of the instrument visualized in the corrected images sequentially generated by the corrector 262 varies within the predetermined range, the controller 21 notifies the operator to keep the X-ray radiation direction to the subject P unchanged.

For example, in the fourth embodiment, an analysis period during which variation in size of the instrument is analyzed is preset. For example, the time equivalent to a plurality of heartbeats is set as this analysis period. For example, the number "N" of frames of corrected images generated after the start of image processing is set as the analysis period. The number "N" of frames is set in accordance with the frame rate of the corrected images, that is, the frame rate of the fluoroscopy mode.

In such a case, the controller 21 acquires the size of the instrument visualized in each of the corrected images in N frames after the start of single-point fixed display, from the detection result of the detector 261. The controller 21 then acquires the maximum value "Lmax" and the minimum value "Lmin" of the length of the instrument during the analysis period. The controller 21 then compares "Lmax−Lmin" with a preset threshold "ThL".

When single-point fixed display in the first embodiment or the third embodiment is performed, the controller 21 can acquire Lmax and Lmin from the distance between the markers. When single-point fixed display in the second embodiment is performed, the controller 21 can acquire Lmax and Lmin from the length of the feature line located in the balloon.

With reference to FIG. 19A and FIG. 19B, a case where the process above is performed when the single-point fixed display in the first embodiment is performed is described. For example, if "Lmax−Lmin>ThL" is satisfied as illustrated in FIG. 19A, the controller 21 causes the display unit 23 to display a message "Change the imaging direction."

For example, if "Lmax−Lmin≤ThL" is satisfied as illustrated in FIG. 19B, the controller 21 causes the display unit 23 to display a message "Keep the imaging direction unchanged." The display position of these messages is, for example, within the display area 200.

Here, the operator referring to the message illustrated in FIG. 19A moves and rotates the C arm 15 and then makes a request again to start image processing (single-point fixed display). The image processor 26 then generates a corrected image again with the changed X-ray radiation direction. The controller 21 then performs the above-described determination process again. These processes are repeatedly performed until a request to terminate image processing (single-point fixed display) is accepted from the operator. In the fourth embodiment, the message may be given by voice.

Figure 20:
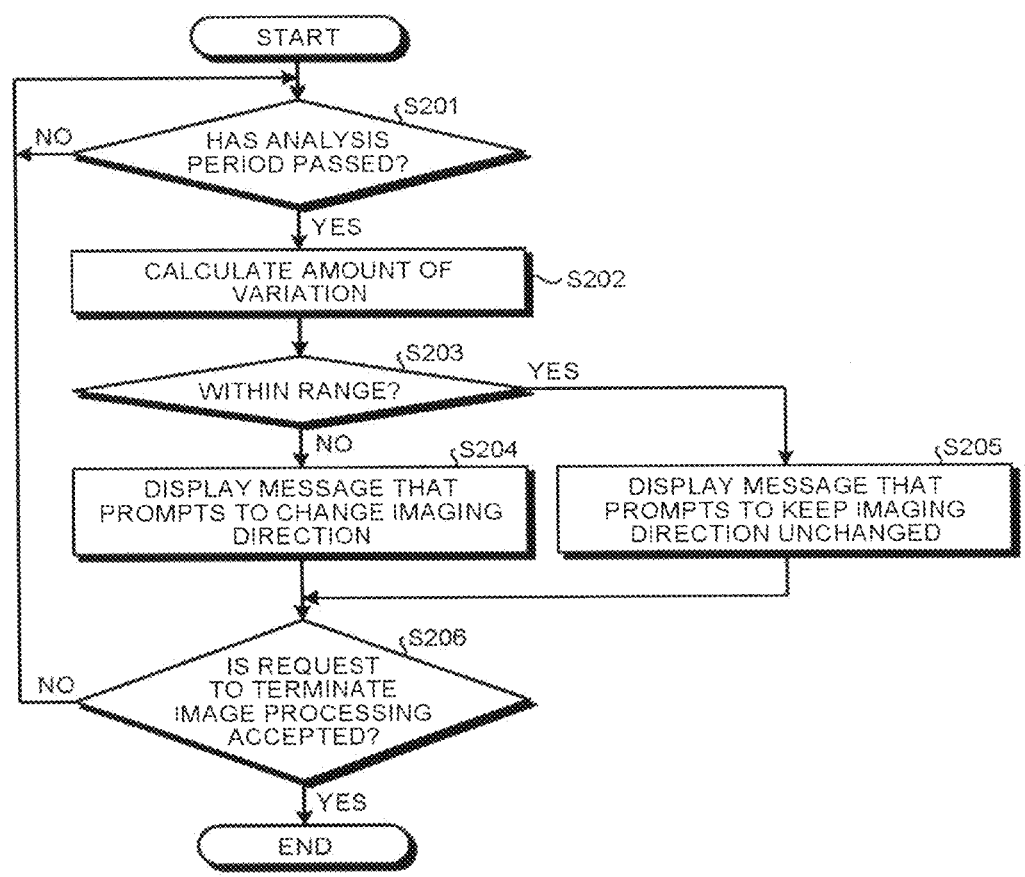
FIG. 20 is a flowchart for explaining an example of a process in an X-ray diagnosis apparatus according to the fourth embodiment.

Referring now to FIG. 20, an example of the process in the X-ray diagnosis apparatus according to the fourth embodiment is described. FIG. 20 is a flowchart for explaining an example of the process in the X-ray diagnosis apparatus according to the fourth embodiment. FIG. 20 is a flowchart illustrating an example of the process performed by the controller 21 after single-point fixed display is started.

As illustrated in FIG. 20, the controller 21 of the X-ray diagnosis apparatus according to the fourth embodiment determines whether the analysis period has passed (step S201). Here, if the analysis period has not passed (No at step S201), the controller 21 waits until the analysis period passes.

If the analysis period has passed (Yes at step S201), the controller 21 calculates the amount of variation (Lmax−Lmin) (step S202). The controller 21 then determines whether the amount of variation falls within the range (step S203). Here, if the amount of variation falls within the range given "Lmax−Lmin≤ThL" (Yes at step S203), the display unit 23 displays a message to prompt the operator to keep the imaging direction unchanged, under the control of the controller 21 (step S205).

On the other hand, if the amount of variation falls outside the range given "Lmax−Lmin>ThL" (No at step S203), the display unit 23 displays a message to prompt the operator to change the imaging direction, under the control of the controller 21 (step S204).

After the processing at step S204 or step S205, the controller 21 determines whether a request to terminate image processing has been accepted (step S206). Here, if a request to terminate image processing has not been accepted (No at step S206), the controller 21 returns to step S201 and determines whether the analysis period has ended. If the process of moving and rotating the C arm 15 is performed as a result of the message given at step S204, the controller 21 makes a determination at step S201 after accepting a request to restart image processing.

On the other hand, if a request to terminate image processing has been accepted (Yes at step S206), the process in the controller 21 ends.

As described above, in the fourth embodiment, whether "Foreshortening" occurs is automatically detected, and the operator is notified of the detection result. The doctor can then change the imaging direction to a direction that does not cause "Foreshortening", and execute endovascular intervention treatment again. Alternatively, the doctor can confirm that the imaging direction is the optimum direction that does not cause "Foreshortening", and proceed to the procedure. The fourth embodiment therefore can further improve the accuracy in positioning the instrument for use in treatment.

Fifth Embodiment

Figure 21A:
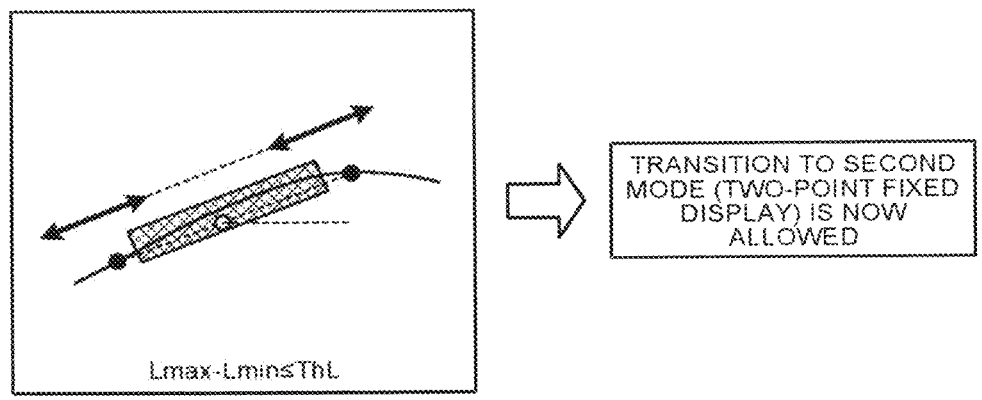
FIG. 21A and FIG. 21B are diagrams for explaining a fifth embodiment.
Figure 21B:
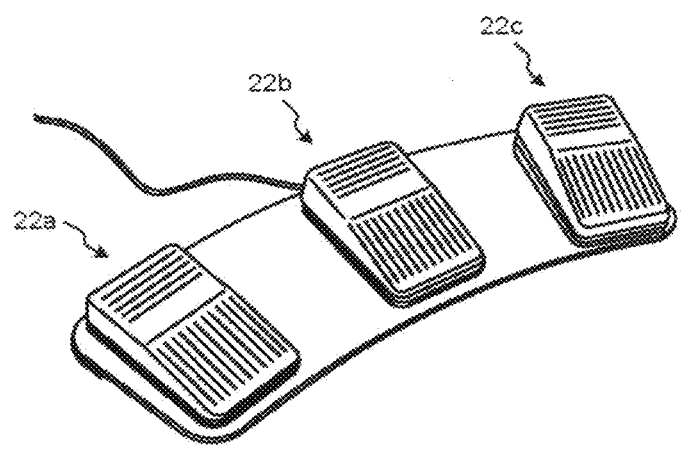

In a fifth embodiment, the image processor 26 can execute the conventional two-point fixed display as well as the single-point fixed display. This case is described with reference to, for example, FIG. 21A and FIG. 21B. FIG. 21A and FIG. 21B are diagrams for explaining the fifth embodiment.

For example, if the imaging direction is changed to a direction that does not cause "Foreshortening", as a result of the notice process by the controller 21 described in the fourth embodiment, the size of the instrument visualized in the original image is substantially constant. If it is confirmed that the imaging direction is the one that does not cause "Foreshortening", as a result of the notice process by the controller 21 described in the fourth embodiment, the size of the instrument visualized in the original image is substantially constant. In such a case, two-point fixed display with the positions of the markers at two points being kept is performed to improve the visibility of a mesh sandwiched between the markers at two points.

Thus, the corrector 262 according to the fifth embodiment has the function of executing a first mode (also referred to as a first correction process mode) in which a corrected image for single-point fixed display is generated as a "first corrected image" and the function of executing a second mode (also referred to as a second correction process mode) in which a corrected image for two-point fixed display is generated as a "second corrected image". In the second mode, the corrector 262 sequentially generates corrected images with the size, position, and inclination of the instrument in the images being kept unchanged, from the X-ray images sequentially generated by the image generator 24.

The controller 21 according to the fifth embodiment gives a notice to prompt the operator to make a transition to the second mode if the size of the instrument visualized in the first corrected images sequentially generated by the corrector 262 in the first mode varies within a predetermined range.

For example, the controller 21 acquires the maximum value "Lmax" and the minimum value "Lmin" of the length of the instrument during the analysis period and compares "Lmax−Lmin" with the threshold "ThL", as described in the fourth embodiment.

If "Lmax−Lmin≤ThL" as illustrated in FIG. 21A, the controller 21 causes the display unit 23 to display a message "Transition to the second mode (two-point fixed display) is now allowed." The display position of such messages is, for example, within the display area 200.

The input unit 22 according to the fifth embodiment has a control unit (also called a switch) for accepting the selection of the first mode or the second mode from the operator. For example, in the fifth embodiment, three footswitches illustrated in FIG. 21B are installed in the vicinity of the table 14. A footswitch 22a illustrated in FIG. 21B is a switch for turning on and off the fluoroscopy mode. The operator may press the footswitch 22a once to turn on the fluoroscopy mode and may press the footswitch 22a once again to turn off the fluoroscopy mode.

A footswitch 22b illustrated in FIG. 21B is a switch for turning on and off the first mode (single-point fixed display). The operator may press the footswitch 22b once to turn on the first mode and may press the footswitch 22b once again to turn off the first mode.

A footswitch 22c illustrated in FIG. 21B is a switch for turning on and off the second mode (two-point fixed display). The operator may press the footswitch 22c once to turn on the second mode and may press the footswitch 22c once again to turn off the second mode.

The operator can turn off the first mode and turn on the second mode by pressing the footswitch 22c once with the first mode ON. The operator can turn off the second mode and turn on the first mode by pressing the footswitch 22b once with the second mode ON. That is, the footswitch 22c switches between the first correction process mode, in which corrected images are sequentially generated based on a single point, and the second correction process mode, in which corrected images are sequentially generated based on the feature points at two points detected in a single X-ray image with the two points being substantially immobile in the corrected images. Such control units allow the doctor as the operator to smoothly switch the first mode and the second mode in a state in the fluoroscopy mode.

For example, when viewing the message "Transition to the second mode (two-point fixed display) is now allowed" appearing on the display unit 23, the doctor recognizes that the imaging direction is the one that does not cause "Foreshortening", and presses the footswitch 22c once to make a transition from the first mode to the second mode.

After a transition is made to the second mode, for example, the second corrected images are displayed as a moving image in the display area 200. Even after a transition is made to the second mode, a variety of display manners illustrated in FIG. 13A to FIG. 13C may be provided. After a transition is made to the second mode, the corrector 262 may generate an addition image or an arithmetic mean image using corrected images corresponding to a plurality of frames and output the generated image to the display unit 23, under the control of the controller 21.

For example, when a corrected image (k) is generated, the corrector 262 generates an arithmetic mean image (k) from the corrected image (k−4) to the corrected image (k) and outputs the arithmetic mean image (k) as the corrected image corresponding to the k-th frame. For example, when a corrected image (k+1) is generated, the corrector 262 generates an arithmetic mean image (k+1) from the corrected image (k−3) to the corrected image (k+1) and outputs the arithmetic mean image (k+1) as the corrected image corresponding to the (k+1)th frame. This processing increases the contrast of the device (such as a mesh) located between the markers at two points, thereby improving the visibility of the device.

Figure 22:
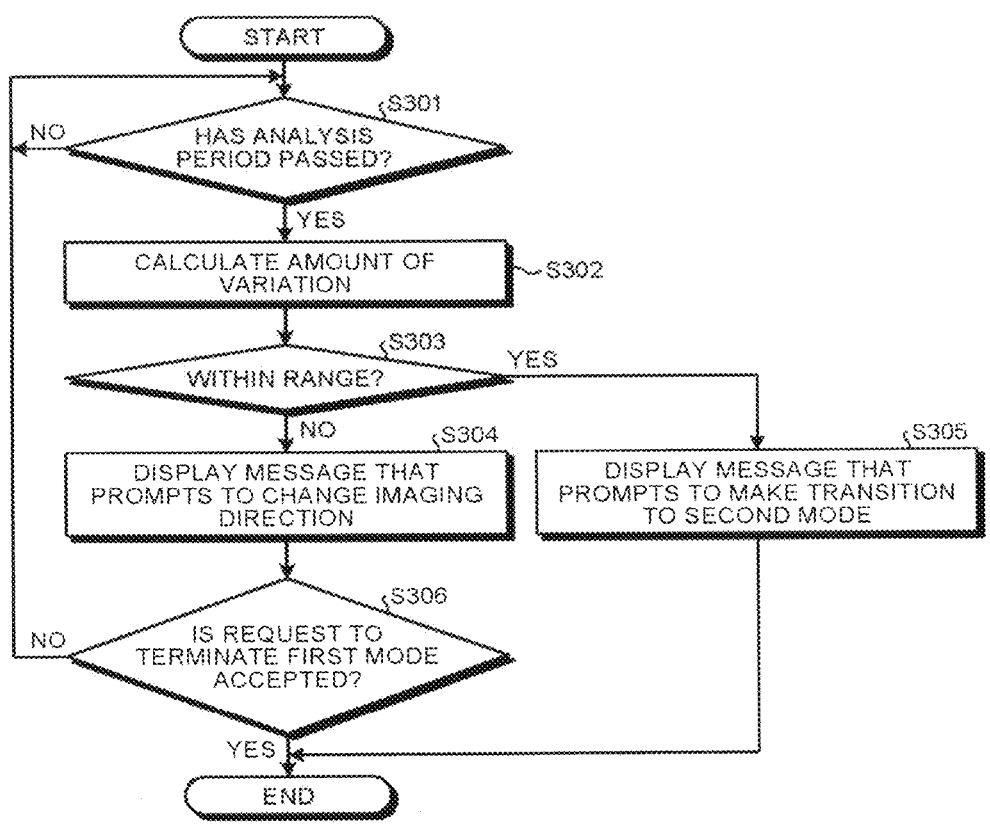
FIG. 22 is a flowchart for explaining an example of a process in an X-ray diagnosis apparatus according to the fifth embodiment.

Referring now to FIG. 22, an example of the process in the X-ray diagnosis apparatus according to the fifth embodiment is described. FIG. 22 is a flowchart for explaining an example of the process in the X-ray diagnosis apparatus according to the fifth embodiment. FIG. 22 is a flowchart illustrating an example of the process performed by the controller 21 after the first mode (single-point fixed display) is started.

As illustrated in FIG. 22, the controller 21 of the X-ray diagnosis apparatus according to the fifth embodiment determines whether the analysis period has passed (step S301). Here, if the analysis period has not passed (No at step S301), the controller 21 waits until the analysis period passes.

On the other hand, if the analysis period has passed (Yes at step S301), the controller 21 calculates the amount of variation (Lmax−Lmin) (step S303). The controller 21 then determines whether the amount of variation falls within the range (step S302). Here, if the amount of variation falls outside the range (No at step S303) given "Lmax−Lmin>ThL", the display unit 23 displays a message to prompt the operator to change the imaging direction, under the control of the controller 21 (step S304).

The controller 21 then determines whether a request to terminate the first mode has been accepted (step S306). Here, if a request to terminate the first mode has not been accepted (No at step S306), the controller 21 returns to step S301 and determines whether the analysis period has ended. If the process of moving and rotating the C arm 15 is performed as a result of the message given at step S304, the controller 21 makes a determination at step S301 after accepting a request to restart the first mode.

If a request to terminate the first mode has been accepted (Yes at step S306), the process in the controller 21 ends.

On the other hand, if the amount of variation falls within the range (Yes at step S303) given "Lmax−Lmin≤ThL", the display unit 23 displays a message to prompt the operator to make a transition to the second mode, under the control of the controller 21 (step S305). The process in the controller 21 then ends.

As described above, in the fifth embodiment, if it is determined that "Foreshortening" does not occur, for example, the operator is prompted to make a transition to the second mode (two-point fixed display), which can provide improved visibility of the mesh sandwiched between the markers at two points. The fifth embodiment therefore can reliably improve the accuracy in positioning the instrument for use in treatment in a state where fluoroscopic imaging is being performed in the optimum imaging direction.

In the fifth embodiment, even after a transition is made to the second mode, the detector 261 may perform the process of detecting a feature pattern for uncorrected X-ray images (original images), and the controller 21 may monitor variation in size of the instrument in the original images. That is, when the amount of variation in size of the instrument in the original images falls outside the range in the second mode, the controller 21 according to the fifth embodiment may determine that "Foreshortening" occurs again because of body movement of the subject P or other reasons and may give a notice to prompt the operator to make a transition to the first mode.

Sixth Embodiment

Although the first to the fifth embodiments have been described above, embodiments other than the foregoing first to fifth embodiments may be carried out in a variety of different forms.

Figure 23:
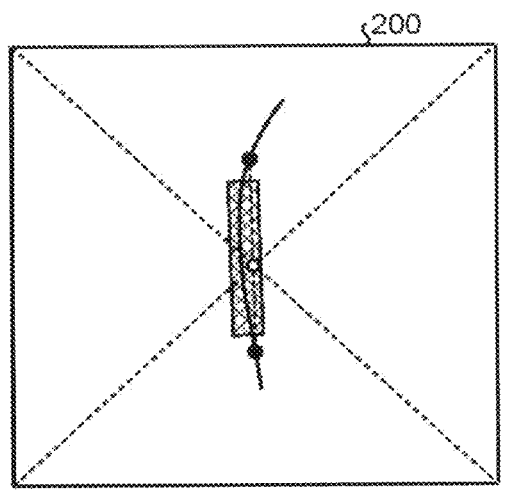
FIG. 23 is a diagram for explaining a modification of the first to the fifth embodiments.

In the description of the foregoing first to fifth embodiments, the angle for single-point fixed display is determined based on the feature pattern in the reference image. However, the corrector 262 may use a preset angle as the angle for single-point fixed display. This modification is described with reference to FIG. 23. FIG. 23 is a diagram for explaining a modification of the first to the fifth embodiments.

In this modification, any angle such as 0 degrees, 45 degrees, or 90 degrees is set as the angle for single-point fixed display. In FIG. 23, a single point for single-point fixed display is set at the center of the display area 200 of the corrected image. In FIG. 23, the angle for single-point fixed display is set at "90 degrees" relative to the horizontal line in the display area 200. That is, in the example illustrated in FIG. 23, the direction of the line connecting the markers at two points visualized in the corrected image is set to the vertical direction in the display area 200. In other words, in the example illustrated in FIG. 23, the direction of the device visualized in corrected images is set to the vertical direction in the display area 200.

In the foregoing modification, since the angle for single-point fixed display can be set to any desired angle, the doctor can proceed to a procedure by referring to a moving image of the corrected images including the visualized device in a direction that allows the doctor to easily grasp the positional relation between the device and the surrounding living tissues.

In the foregoing first to fifth embodiments and modifications, single-point fixed display is performed in endovascular intervention treatment. However, the single-point fixed display described in the foregoing first to fifth embodiments and modification can be applied to any treatment as long as the treatment is performed by inserting an instrument into a subject P and referring to an X-ray image.

In the foregoing fourth embodiment, whether "Foreshortening" occurs is detected in a state where single-point fixed display is being performed, and the operator is notified of the detection result. The X-ray diagnosis apparatus according to an embodiment may present the imaging direction that does not cause "Foreshortening", if the occurrence of "Foreshortening" is detected in a state where single-point fixed display is being performed.

Specifically, if the size of the instrument visualized in the corrected images sequentially generated by the corrector 262 varies outside the predetermined range, the controller 21 gives a notice to the operator to rotate the C arm 15 supporting the X-ray tube 12 such that the X-ray tube 12 is arranged at a position to which the X-ray tube 12 is rotated around the direction in which the size of the instrument varies. For example, the controller 21 gives a notice to the operator to rotate the C arm 15 such that the X-ray tube 12 is arranged at a position to which the X-ray tube 12 is rotated approximately 90 degrees around the direction in which the size of the instrument varies.

Here, the imaging direction that does not cause "Foreshortening" is described with reference to FIG. 24. FIG. 24 is a diagram for explaining an example of changing an imaging direction according to the sixth embodiment. FIG. 24(A) illustrates the imaging direction that causes "Foreshortening" and FIG. 24(B) illustrates the imaging direction that does not cause "Foreshortening". For example, as illustrated in FIG. 24(A), "Foreshortening" occurs in such a manner that the length of the device in the image appears to expand and contract as indicated by an arrows 51 because the degree of the "oblique relation" of the line segment M5&M6 including stent markers M5 and M6 changes relative to the X-ray radiation direction indicated by an arrow 41.

The controller 21 according to the sixth embodiment then gives a notice to the operator to rotate the C arm 15 so as to change the X-ray radiation direction to the direction of an arrow 42 as illustrated in FIG. 24(B). For example, when the device (the line segment M5&M6) in the subject moves as illustrated in FIG. 24(A), the radiation of X-rays in the direction of the arrow 41 causes "Foreshortening" as described above. However, if X-rays are applied in the direction of the arrow 42, the motion of the device among X-ray images is merely rotational movement as indicated by an arrow 52, as illustrated in FIG. 24(B), so that the correction process described above is performed to allow single-point fixed display in which "Foreshortening" does not occur.

The controller 21 gives a notice to the operator to rotate the C arm 15 so as to change the X-ray radiation direction from the arrow 41 to the arrow 42 by moving the X-ray radiation position to the position rotated around the expanding/contracting direction shown by the arrow 51. Here, the X-ray radiation direction is not limited to the direction of the arrow 42, and X-rays may be applied from the opposite direction. For example, when X-rays are applied from below to above in FIG. 24(B), the motion of the device among X-ray images merely includes rotational movement as indicated by the arrows 52. The controller 21 therefore gives a notice to the operator to rotate the C arm 15 so as to move the X-ray radiation position to a position to which the X-ray radiation position is rotated in either direction around the device expanding and contracting directions. In other words, the controller 21 gives a notice to rotate the C arm 15 so as to apply X-rays in either of the directions perpendicular to the line segment connecting the stent markers in the image.

For example, the controller 21 notifies the operator by displaying information about the rotation of the C arm in the display area 200 in which the corrected images are displayed as a moving image. Here, the controller 21 may notify the operator of the direction to rotate the C arm, as information about the rotation of the C arm, or may notify the operator of the direction and the angle. For example, in a case where the C arm 15 is located at a position "LAO (Left Anterior Oblique): 0 deg." and "CRA (cranial): 0 deg." at present and the stent markers expand and contract horizontally on the screen, the controller 21 gives a notice in the display area 200 to rotate the C arm 15 in the "CRA" or "CAU (caudal)" direction.

The operator can gradually reduce the expansion and contraction of the device in the image by rotating the C arm 15 in the "CRA" or "CAU" direction displayed in the display area 200. The controller 21 can also display the angle by which to rotate, in addition to the direction described above. For example, the controller 21 displays a notice in the display area 200 to rotate the C arm 15 in the "CRA" or "CAU" direction by "90 deg." In such a case, the operator can rotate the C arm 15 in the "CRA" or "CAU" direction by "90 deg." by performing an operation (for example, pressing a button) through the input unit 22.

The examples above are given only by way of illustration. The stent markers may not be horizontal on the screen. In such a case, the controller 21 displays a notice in the display area to rotate the C arm 15 in the "CRA", "CAU", "LAO", or "RAO (Right Anterior Oblique)" direction so as to apply X-rays from either of the directions perpendicular to the line segment connecting the stent markers in the image.

Here, the information about the rotation of the C arm may be a schematic representation of the C arm or may be represented by characters and numerals. Even when the operation of rotating the C arm 15 described above is performed, the expansion and contraction of the device may not be eliminated. Thus, the controller 21 continuously detects whether "Foreshortening" occurs even after the C arm 15 is rotated through the operation by the operator, and if the occurrence of "Foreshortening" is detected, the controller 21 performs control such that information about the rotation of the C arm is displayed again.

In the foregoing first to fifth embodiments, stent markers are used as feature points. However, the feature points according to embodiments of this application are not limited to stent markers and may be a pattern of the stent strut or others. An example is described with reference to FIG. 13C. For example, as illustrated in the right diagram in FIG. 13C, after the stent strut is retained through single-point fixed display using stent markers, the X-ray diagnosis apparatus performs fixed display of the stent strut using the pattern of the stent strut as a feature point. That is, the detector 261 sequentially detects the pattern of the retained stent strut in the X-ray images sequentially generated after the catheter having a stent marker is removed. The corrector 262 sequentially generates corrected images as described above, using the pattern of the stent strut detected by the detector 261 as a feature pattern. The controller 21 sequentially displays the corrected images sequentially generated by the corrector 262 on the display unit 23.

In the foregoing first to Sixth embodiments and modification, single-point fixed display is performed in the X-ray diagnosis apparatus. However, the single-point fixed display described in the foregoing first to Sixth embodiments and modification may be performed in an image processing apparatus installed independently of the X-ray diagnosis apparatus and having the functions of the image processor 26 and the controller 21. In such a case, the image processing apparatus receives time-series data of X-ray images received from the X-ray diagnosis apparatus, a database of a PACS, or a database of an electronic health record system and then executes the image processing method described above.

As described above, the first to the Sixth embodiments and modification can assist in improving the accuracy in positioning an instrument for use in treatment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
an image generator that sequentially generates X-ray images based on X-rays emitted from an X-ray tube and transmitted through a subject;
a detector that detects a position of a feature point in the sequentially generated X-ray images;
a corrector that performs a correction process such that an angle of a line segment including a first position of the feature point and a position of a first single point based on the first position of the feature point detected in any one of the sequentially generated X-ray images substantially agree with an angle based on a second position of the feature point and a position of a second single point based on the second position of the feature point detected in a new X-ray image generated after the sequentially generated X-ray images, thereby sequentially generating corrected images in which a point different from the feature point in the images is located at substantially the same position; and
a controller that, every time each of the corrected images is newly generated by the corrector, sequentially displays the corrected images, thereby displaying a moving image on a display.

2. The X-ray diagnosis apparatus according to claim 1, wherein
the detector detects positions of two feature points in a single X-ray image, and
the corrector performs the correction process using,
as the position of the first single point based on the first position of the feature point, a position of an approximate midpoint of two feature points detected in the X-ray image by the detector; and
as the position of the second single point based on the second position of the feature point, a position of an approximate midpoint of two feature points detected in the new X-ray image by the detector.

3. The X-ray diagnosis apparatus according to claim 1, further comprising a switch that switches a correction process mode,
the detector detects positions of two feature points in a single X-ray image; and
the switch that switches between a first correction process mode, in which corrected images are sequentially generated based on the single point, and a second correction process mode, in which corrected images are sequentially generated, based on the two feature points detected in a single X-ray image, with the two feature points being substantially immobile in the corrected images.

4. The X-ray diagnosis apparatus according to claim 1, wherein the corrector sequentially generates the corrected images by performing the correction process between frames in the sequentially generated X-ray images.

5. The X-ray diagnosis apparatus according to claim 1, wherein the controller determines whether the size of an instrument visualized in each of the corrected images sequentially generated by the corrector falls within a predetermined range or outside the range, and notifies an operator of a detection result.

6. The X-ray diagnosis apparatus according to claim 5, wherein if the size of the instrument visualized in the respective corrected images sequentially generated by the corrector varies outside the predetermined range, the controller gives a notice to prompt the operator to change an X-ray radiation direction to the subject.

7. The X-ray diagnosis apparatus according to claim 5, wherein if the size of the instrument visualized in the respective corrected images sequentially generated by the corrector varies within the predetermined range, the controller notifies the operator to keep an X-ray radiation direction to the subject unchanged.

8. The X-ray diagnosis apparatus according to claim 1, wherein
the detector detects positions of two feature points in a single X-ray image,
the corrector has a function of executing a first correction process mode, in which corrected images are sequentially generated based on the single point, and a function of executing a second correction process mode, in which corrected images are sequentially generated, based on the two feature points detected in one of the single X-ray images, with the two feature points being substantially immobile in the corrected images, and
if the size of an instrument visualized in the respective corrected images sequentially generated by the corrector in the first correction process mode varies within a predetermined range, the controller gives a notice to prompt a transition to the second correction process mode.

9. The X-ray diagnosis apparatus according to claim 1, wherein the feature point is a balloon marker inserted into the subject.

10. The X-ray diagnosis apparatus according to claim 1, wherein the corrector performs either a translation process or a rotation process or these processes without performing a rescale process to generate the corrected images from X-ray images to be corrected.

11. The X-ray diagnosis apparatus according to claim 1, wherein
the detector detects a position of a single feature point of an instrument and a linear feature line of the instrument, and
the corrector uses a position of a single point defined by the position of the single feature point detected in the X-ray image as the position of the first single point based on the first position of the feature point and uses an angle between the feature line detected in the X-ray image and a reference line in the X-ray image as the angle of the line segment, and
uses a position of a single point defined by the position of the single feature point detected in the new X-ray image as the position of the second single point based on the second position of the feature point and uses an angle between the feature line detected in the new X-ray image and a reference line in the new X-ray image as the angle of the line segment.

12. The X-ray diagnosis apparatus according to claim 1, wherein
the detector detects positions of at least three feature points of an instrument or a plurality of instruments, and
the corrector uses a position of a single point defined by at least one of the at least three feature points detected in the X-ray image as the position of the first single point based on the first position of the feature point and uses an angle between a line segment connecting at least two of the at least three feature points detected in the X-ray image and a reference line in the X-ray image as the angle of the line, and
uses a position of a single point defined by at least one of the at least three feature points detected in the new X-ray image as the position of the second single point based on the second position of the feature point and uses an angle between a line segment connecting at least two of the at least three feature points detected in the new X-ray image and a reference line in the new X-ray image as the angle of the line.

13. The X-ray diagnosis apparatus according to claim 10, wherein the corrector uses a preset single point as the single point based on the feature point.

14. The X-ray diagnosis apparatus according to claim 10, wherein the corrector uses a preset angle as the angle of the line segment.

15. The X-ray diagnosis apparatus according to claim 1, wherein the controller performs control for displaying the corrected images as a moving image and control for displaying, as a moving image, X-ray images sequentially generated by the image generator.

16. The X-ray diagnosis apparatus according to claim 1, wherein the controller performs control for displaying, as a moving image, a predetermined area including an instrument in the corrected images or control for displaying, as a moving image, enlarged images in which the predetermined area is enlarged.

17. The X-ray diagnosis apparatus according to claim 5, wherein if the size of the instrument visualized in the respective corrected images sequentially generated by the corrector varies outside the predetermined range, the controller gives a notice to the operator to rotate an arm supporting the X-ray tube such that the X-ray tube is arranged at a position to which the X-ray tube is rotated around a direction in which the size of the instrument varies.

18. The X-ray diagnosis apparatus according to claim 17, wherein the controller gives a notice to the operator to rotate the arm such that the X-ray tube is arranged at a position to which the X-ray tube is rotated approximately 90 degrees around a direction in which the size of the instrument varies.

19. An X-ray diagnosis apparatus comprising:
- an image generator that sequentially generates X-ray images based on X-rays emitted from an X-ray tube and transmitted through a subject;
- a detector that detects a position of a feature point in the sequentially generated X-ray images;
- a corrector that performs a correction process such that an angle of a line segment including a first position of the feature point and a position of a first single point of the first position of the feature point detected in any one of the sequentially generated X-ray images substantially agree with an angle based on a second position of the feature point and a position of a second single point of the second position of the feature point detected in a new X-ray image generated after the sequentially generated X-ray images, thereby sequentially generating corrected images in which a point different from the feature point in the images is located at substantially the same position; and
- a controller that, every time each of the corrected images is newly generated by the corrector, sequentially displays the corrected images, thereby displaying a moving image on a display.

20. An image processing apparatus comprising:
- a detector that detects a position of a feature point in X-ray images sequentially generated based on X-rays emitted from an X-ray tube and transmitted through a subject;
- a corrector that performs a correction process such that an angle of a line segment including a first position of the feature point and a position of a first single point based on the first position of the feature point detected in any one of the sequentially generated X-ray images substantially agree with an angle based on a second position of the feature point and a position of a second single point based on the second position of the feature point detected in a new X-ray image generated after the sequentially generated X-ray images, thereby sequentially generating corrected images in which a point different from the feature point in the images is located at substantially the same position; and
- a controller that, every time each of the corrected images is newly generated by the corrector, sequentially displays the corrected images, thereby displaying a moving image on a display.

* * * * *